United States Patent
Chun et al.

(10) Patent No.: US 11,078,525 B2
(45) Date of Patent: Aug. 3, 2021

(54) DETECTION OF TARGET NUCLEIC ACID SEQUENCE BY PTO CLEAVAGE AND EXTENSION-DEPENDENT CLEAVAGE

(75) Inventors: Jong Yoon Chun, Seoul (KR); Young Jo Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 44 days.

(21) Appl. No.: 14/008,096

(22) PCT Filed: Mar. 29, 2012

(86) PCT No.: PCT/KR2012/002331
§ 371 (c)(1),
(2), (4) Date: Sep. 27, 2013

(87) PCT Pub. No.: WO2012/134195
PCT Pub. Date: Oct. 4, 2012

(65) Prior Publication Data
US 2014/0057264 A1 Feb. 27, 2014

(30) Foreign Application Priority Data
Mar. 29, 2011 (KR) .................. 10-2011-0028345

(51) Int. Cl.
*C12P 19/34* (2006.01)
*C12Q 1/6823* (2018.01)
(Continued)

(52) U.S. Cl.
CPC ......... *C12Q 1/6823* (2013.01); *C12Q 1/6834* (2013.01); *C12Q 1/6853* (2013.01)

(58) Field of Classification Search
USPC ............ 435/6.1, 6.11, 6.12, 91.1, 91.2, 183; 436/94, 501; 536/23.1, 24.3, 24.33, 25.3
See application file for complete search history.

(56) References Cited

U.S. PATENT DOCUMENTS

| 5,210,015 A | 5/1993 | Gelfand et al. |
| 5,326,145 A | 7/1994 | Lee |

(Continued)

FOREIGN PATENT DOCUMENTS

| EP | 1564306 A2 | 8/2005 |
| EP | 2256216 A1 | 1/2010 |

(Continued)

OTHER PUBLICATIONS

Lambda Exonuclease from thermofisher.com/order/catalog/product/EN0561. Printed on Nov. 16, 2015.*

(Continued)

*Primary Examiner* — Frank W Lu
(74) *Attorney, Agent, or Firm* — Gianna Julian-Arnold; Saul Ewing Arnstein & Lehr LLP

(57) ABSTRACT

The present invention relates to the detection of a target nucleic acid sequence by a PCEC (PTO Cleavage and Extension-Dependent Cleavage) assay. The present invention is characterized by generating a cleavage site for a nucleolytic enzyme on the extended duplex of which the formation is dependent on the presence of a target nucleic acid sequence. The present invention detects the occurrence of the cleavage of the extended duplex, thereby determining the presence of the target nucleic acid sequence.

8 Claims, 10 Drawing Sheets

Specification includes a Sequence Listing.

(51) Int. Cl.
*C12Q 1/6834* (2018.01)
*C12Q 1/6853* (2018.01)

(56) References Cited

U.S. PATENT DOCUMENTS

| | | | |
|---|---|---|---|
| 5,538,848 | A | 7/1996 | Livak et al. |
| 5,691,142 | A | 11/1997 | Dahlberg et al. |
| 6,893,819 | B1 | 5/2005 | Sorge |
| 7,381,532 | B2 | 6/2008 | Sorge |
| 2002/0045738 | A1 | 4/2002 | Singh et al. |
| 2003/0077608 | A1 | 4/2003 | Coull et al. |
| 2004/0191823 | A1 | 9/2004 | Virgos et al. |
| 2005/0142595 | A1 | 6/2005 | Maletta et al. |
| 2005/0221315 | A1 | 10/2005 | Braven et al. |
| 2006/0110748 | A1 | 5/2006 | Sorge |
| 2006/0246469 | A1 | 11/2006 | Sorge |
| 2007/0099211 | A1 | 5/2007 | Aivazachvili et al. |
| 2007/0231815 | A1 | 10/2007 | Sorge |
| 2008/0131890 | A1 | 6/2008 | Allawi et al. |
| 2008/0160535 | A1 | 7/2008 | Gold et al. |
| 2008/0193940 | A1 | 8/2008 | Aivazachvili et al. |
| 2008/0241838 | A1 | 10/2008 | Scaboo et al. |
| 2009/0305237 | A1 | 12/2009 | Cantor et al. |
| 2010/0041049 | A1 | 2/2010 | Smith et al. |
| 2011/0136118 | A1 | 6/2011 | Kreader et al. |
| 2011/0281266 | A1 | 11/2011 | Sergeev et al. |
| 2012/0220468 | A1 | 8/2012 | Chun et al. |

FOREIGN PATENT DOCUMENTS

| | | | |
|---|---|---|---|
| JP | 2003334097 | | 11/2003 |
| JP | 2004305219 | A | 11/2004 |
| JP | 2008193911 | | 2/2007 |
| KR | 1020090067334 | A | 6/2009 |
| WO | 1998023774 | | 6/1998 |
| WO | 2005010199 | A2 | 2/2005 |
| WO | 2005059548 | A1 | 6/2005 |
| WO | 2006004949 | A1 | 1/2006 |
| WO | 2006005081 | A2 | 1/2006 |
| WO | 2008076948 | A1 | 6/2008 |
| WO | 2008094902 | A2 | 8/2008 |
| WO | 2008102057 | A1 | 8/2008 |
| WO | 2009117327 | A2 | 10/2009 |
| WO | 2010055134 | A1 | 5/2010 |
| WO | 2010128041 | A1 | 11/2010 |
| WO | 2011028041 | A2 | 3/2011 |
| WO | 2011078441 | A1 | 6/2011 |
| WO | 2012096523 | A2 | 7/2012 |
| WO | 2012134195 | A2 | 10/2012 |
| WO | 2013115442 | A1 | 8/2013 |

OTHER PUBLICATIONS

Nurmi et al, A new label technology for the detection of specific polymerase chain reaction products in a closed tube. Nucleic Acids Research, 28, e280, 2000.*
Lambda Exonuclease from New England Biolabs. Printd on Jun. 12, 2017.*
T5 exonuclease from New England Biolabs, Printed on Jun. 11, 2018.*
"Exonuclease VIII, truncated" from New England Biolabs. Printed on Dec. 14, 2018.*
Lohmann et al. A new enzymatic route for production of long 5'-phosphorylated oligonucleotides using suicide cassettes and rolling circle DNA synthesis. BMC Biotechnology. 2007, vol. 7, No. 49.
Hessner et al. Genotyping of Factor V G1691A (Leiden) without the Use of PCR by Invasive Cleavage of Oligonucleotide Probes. Clinical Chemistry. vol. 46, No. 8, pp. 1051-1056.
International Search Report, dated Oct. 31, 2012, issued in priority International Application No. PCT/KR2012/002331.
Lyamichev, V., et al.; Polymorphism identification and quantitative detection of genomic DNA by invasive cleavage of oligonucleotide probes; 1999 Nature America Inc., Nature Biotechnology, vol. 17, Mar. 1999, pp. 292-296.
Olivier, M.; the Invader® assay of SNP genotyping; Elsevier, Mutation Research, vol. 573, 2005, pp. 103-110.
Roux, P., et al.; Direct Measurement of Multiple mRNAs in Nerve Growth Factor-Induced PC12 Cells Using Electrophoretic Tags to Monitor Biomarkers of Neuronal Differentiation in 96-Well Format; Assay and Drug Development Technologies, vol. 2, No. 6, 2004, pp. 637-646.
Allawi, H., et al.; Quantitation of microRNAs using a modified Invader assay; RNA Society, vol. 10, 2004, pp. 1153-1161.
Yuan, Y., et al.; Establishment of a Modified High Resolution Melting Assay Based on Allele-specific-extension to Determine Single Nucleotide Polymorphism; Journal of Capital Medical University, vol. 31, No. 6, Dec. 2010, pp. 742-747 [Abstract].

* cited by examiner

A. Probing and Tagging Oligonucleotide (PTO)

B. Capturing and Templating Oligonucleotide (CTO)

A. Hybridization

B. Primer extension & Cleavage of PTO

C. Hybridization to CTO & Extension of PTO fragment

D. Cleavage by 5' to 3' exonuclease & Detection

A. Hybridization

B. Primer extension & Cleavage of PTO

C. Hybridization to CTO & Extension of PTO fragment

D. Cleavage by restriction enzyme & Detection

A. Hybridization

B. Primer extension & Cleavage of PTO

C. Hybridization to CTO & Extension of PTO fragment

D. Cleavage by RNase H & Detection

A. Hybridization

B. Primer extension & Cleavage of PTO

C. Hybridization to CTO & Extension of PTO fragment

D. Cleavage by 5' to 3' exonuclease & Detection

A. Hybridization

B. Primer extension & Cleavage of PTO

C. Hybridization to CTO & Extension of PTO fragment

D. Cleavage by Restriction enzyme & Detection

A. Hybridization

B. Primer extension & Cleavage of PTO

C. Hybridization to CTO & Extension of PTO fragment

D. Cleavage by RNase H & Detection

A. Hybridization

B. Primer extension & Cleavage of PTO

C. Hybridization to CTO & Extension of PTO fragment

D. Cleavage by Restriction enzyme & Detection

A. Hybridization

B. Primer extension & Cleavage of PTO

C. Hybridization to CTO & Extension of PTO fragment

Solid support

D. Cleavage by RNase H & Detection

Target detection using PCEC assay

| Template [1] | PTO [2] | CTO [3] | Ct |
|---|---|---|---|
| + | + | + | 5.43 |
| - | + | + | - |
| + | - | + | - |
| + | + | - | - |

[1] Template is a synthetic oligonucleotide for *Neisseria gonorrhoeae* gene.
[2] PTO (Probing and Tagging Oligonucleotide) is blocked with a carbon spacer at its 3'-end.
[3] CTO (Capturing and Templating Oligonucleotide) has a fluorescent reporter molecule and a quencher molecule in the templating portion.

SEQUENCE LISTING

```
<160> NUMBER OF SEQ ID NOS: 6

<210> SEQ ID NO 1
<211> LENGTH: 86
<212> TYPE: DNA
<213> ORGANISM: Artificial Sequence
<220> FEATURE:
<223> OTHER INFORMATION: Neisseria gonorrhoeae synthetic template (NG-T)

<400> SEQUENCE: 1
aaatatgcga aacacgccaa tgaggggcat gatgctttct ttttgttctt gctcggcaga    60
gcgagtgata ccgatccatt gaaaaa                                         86

<210> SEQ ID NO 2
<211> LENGTH: 21
<212> TYPE: DNA
<213> ORGANISM: Artificial Sequence
<220> FEATURE:
<223> OTHER INFORMATION: Neisseria gonorrhoeae upstream primer (NG-R)

<400> SEQUENCE: 2
caatggatcg gtatcactcg c                                              21

<210> SEQ ID NO 3
<211> LENGTH: 40
<212> TYPE: DNA
<213> ORGANISM: Artificial Sequence
<220> FEATURE:
<223> OTHER INFORMATION: Neisseria gonorrhoeae probing and tagging
        oligonucleotide 1 (NG-PTO-1)
```

-continued

```
<400> SEQUENCE: 3
acgacggcta ggctttactg cccctcattg gcgtgtttcg                    40

<210> SEQ ID NO 4
<211> LENGTH: 36
<212> TYPE: DNA
<213> ORGANISM: Artificial Sequence
<220> FEATURE:
<223> OTHER INFORMATION: Neisseria gonorrhoeae capturing and templating
      oligonucleotide 1 (NG-CTO-1)

<400> SEQUENCE: 4
cctcctcctc ctcctccagt aaagcctagc cgtcgt                        36

<210> SEQ ID NO 5
<211> LENGTH: 32
<212> TYPE: DNA
<213> ORGANISM: Artificial Sequence
<220> FEATURE:
<223> OTHER INFORMATION: Neisseria gonorrhoeae probing and tagging
      oligonucleotide 2 (NG-PTO-2)

<400> SEQUENCE: 5
acgacggctt ggcccctcat tggcgtgttt cg                            32

<210> SEQ ID NO 6
<211> LENGTH: 42
<212> TYPE: DNA
<213> ORGANISM: Artificial Sequence
<220> FEATURE:
<223> OTHER INFORMATION: Neisseria gonorrhoeae capturing and templating
      oligonucleotide 2 (NG-CTO-2)

<400> SEQUENCE: 6
cctcctggcc ctcctcctcc tccagtaaag ccaagccgtc gt                 42
```

DETECTION OF TARGET NUCLEIC ACID SEQUENCE BY PTO CLEAVAGE AND EXTENSION-DEPENDENT CLEAVAGE

CROSS REFERENCE TO RELATED APPLICATIONS

This application claims the priority of PCT/KR2012/002331, filed on Mar. 29, 2012, which claims the benefit of priority to Korean Application No, 10-2011-0028345, filed on Mar. 29, 2011, the entire contents of each of which are hereby incorporated in total by reference.

SEQUENCE LISTING

This application incorporates by reference the Sequence Listing contained in an ASCII text file named "361406-00017_Seq_List.txt" submitted via EFS-Web. The text file was created on Oct. 22, 2013, and is 1.91 kb in size.

BACKGROUND OF THE INVENTION

Field of the Invention

The present invention relates to the detection of a target nucleic acid sequence by a PCEC (PTO Cleavage and Extension-Dependent Cleavage) assay.

Description of the Related Art

DNA hybridization is a fundamental process in molecular biology and is affected by ionic strength, base composition, length of fragment to which the nucleic acid has been reduced, the degree of mismatching, and the presence of denaturing agents. DNA hybridization-based technologies would be a very useful tool in specific nucleic acid sequence determination and clearly be valuable in clinical diagnosis, genetic research, and forensic laboratory analysis.

However, the conventional methods and processes depending mostly on hybridization are very likely to produce false positive results due to non-specific hybridization between probes and non-target sequences. Therefore, there remain problems to be solved for improving their reliability.

Besides probe hybridization processes, several approaches using additional enzymatic reactions, for example, TaqMan™ probe method, have been suggested.

In TaqMan™ probe method, the labeled probe hybridized with a target nucleic acid sequence is cleaved by a 5' nuclease activity of an upstream primer-dependent DNA polymerase, generating a signal indicating the presence of a target sequence (U.S. Pat. Nos. 5,210,015, 5,538,848 and 6,326,145). The TaqMan™ probe method suggests two approaches for signal generation: polymerization-dependent cleavage and polymerization-independent cleavage. In polymerization-dependent cleavage, extension of the upstream primer must occur before a nucleic acid polymerase encounters the 5'-end of the labeled probe. As the extension reaction continues, the polymerase progressively cleaves the 5'-end of the labeled probe. In polymerization-independent cleavage, the upstream primer and the labeled probe are hybridized with a target nucleic acid sequence in close proximity such that binding of the nucleic acid polymerase to the 3'-end of the upstream primer puts it in contact with the 5'-end of the labeled probe to release the label. In addition, the TaqMan™ probe method discloses that the labeled probe at its 5'-end having a 5'-tail region not-hybridizable with a target sequence is also cleaved to form a fragment comprising the 5'-tail region.

There have been reported some methods in which a probe having a 5'-tail region non-complementary to a target sequence is cleaved by 5' nuclease to release a fragment comprising the 5'-tail region.

For instance, U.S. Pat. No. 5,691,142 discloses a cleavage structure to be digested by 5' nuclease activity of DNA polymerase. The cleavage structure is exemplified in which an oligonucleotide comprising a 5' portion non-complementary to and a 3' portion complementary to a template is hybridized with the template and an upstream oligonucleotide is hybridized with the template in close proximity. The cleavage structure is cleaved by DNA polymerase having 5' nuclease activity or modified DNA polymerase with reduced synthetic activity to release the 5' portion non-complementary to the template. The released 5' portion is then hybridized with an oligonucleotide having a hairpin structure to form a cleavage structure, thereby inducing progressive cleavage reactions to detect a target sequence.

U.S. Pat. No. 7,381,532 discloses a process in which the cleavage structure having the upstream oligonucleotide with blocked 3'-end is cleaved by DNA polymerase having 5' nuclease activity or FEN nuclease to release non-complementary 5' flap region and the released 5' flap region is detected by size analysis or interactive dual label. U.S. Pat. No. 6,893,819 discloses that detectable released flaps are produced by a nucleic acid synthesis dependent, flap-mediated sequential amplification method. In this method, a released flap from a first cleavage structure cleaves, in a nucleic acid synthesis dependent manner, a second cleavage structure to release a flap from the second cleavage structure and the release flaps are detected.

U.S. Pat. Appln. Pub. 2008-0241838 discloses a target detection method using cleavage of a probe having a 5' portion non-complementary to a target nucleic acid sequence and hybridization of a capture probe. A label is positioned on the non-complementary 5' portion. The labeled probe hybridized with the target sequence is cleaved to release a fragment, after which the fragment is then hybridized with the capture probe to detect the presence of the target sequence. In this method, it is necessary that an uncleaved/intact probe is not hybridized with the capture probe. For that, the capture probe having a shorter length has to be immobilized onto a solid substrate. However, such a limitation results in lower efficiency of hybridization on a solid substrate and also in difficulties in optimization of reaction conditions.

Therefore, there remain long-felt needs in the art to develop novel approaches for detection of a target sequence, preferably multiple target sequences, in a liquid phase and on a solid phase by not only hybridization but also enzymatic reactions such as 5' nucleolytic reaction in a more convenient, reliable and reproducible manner. Furthermore, a novel target detection method not limited by the number of types of labels (particularly, fluorescent labels) is also needed in the art.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel approaches to detect target sequences with more improved accuracy and convenience, inter alia, in a multiplex manner. As a result, we have established novel protocols for detection of target sequences in which target detection is accomplished by not only probe hybridization but also successive cleavage reactions, 5' nucleolytic reaction of the PTO and nucleolytic reaction of the extended duplex. The present protocols are well adopted to liquid phase reactions as well as solid phase reactions, and ensure detection of multiple target sequences with more improved accuracy and convenience.

Accordingly, it is an object of this invention to provide a method for detecting a target nucleic acid sequence from a DNA or a mixture of nucleic acids by a PCEC (PTO Cleavage and Extension-Dependent Cleavage) assay.

It is another object of this invention to provide a kit for detecting a target nucleic acid sequence from a DNA or a mixture of nucleic acids by a PCEC (PTO Cleavage and Extension-Dependent Cleavage) assay.

Other objects and advantages of the present invention will become apparent from the detailed description to follow taken in conjugation with the appended claims and drawings.

BRIEF DESCRIPTION OF THE DRAWINGS

FIG. 1A shows the schematic structures of PTO). FIG. 1B shows the schematic structures of CTO.

FIG. 2A shows hybridization. FIG. 2B shows primer extension and cleavage of PTO. FIG. 2C shows hybridization to CTO and Extension of PTO fragment. FIG. 2D shows cleavage by 5' to 3' exonuclease and detection. The CTO has a reporter molecule and a quencher molecule at its templating portion.

(FIG. 3A shows hybridization. FIG. 3B shows primer extension and cleavage of PTO. FIG. 3C shows hybridization to CTO and extension of PTO fragment. FIG. 3D shows cleavage by restriction enzyme and detection). The CTO has a reporter molecule and a quencher molecule at its templating portion.

(FIG. 4A shows hybridization. FIG. 4B shows primer extension and cleavage of PTO. FIG. 4C shows hybridization to CTO and extension of PTO fragment; FIG. 4D shows cleavage by RNase H and detection. The CTO has a reporter molecule and a quencher molecule at its templating portion.

FIG. 5A shows hybridization. FIG. 5B shows primer extension and cleavage of PTO. FIG. 5C shows hybridization to CTO and extension of PTO fragment. FIG. 5D shows cleavage by 5' to 3' exonuclease and detection). The CTO has a fluorescent single label at its templating portion. The CTO is immobilized on a solid substrate through its 3'-end.

FIG. 6A shows hybridization. FIG. 6B shows primer extension and cleavage of PTO. FIG. 6C shows hybridization to CTO and extension of PTO fragment. FIG. 6D shows cleavage by restriction enzyme and detection. The CTO has a fluorescent single label at its capturing portion. The CTO is immobilized on a solid substrate through its 5'-end.

FIG. 7A shows hybridization. FIG. 7B shows primer extension and cleavage of PTO. FIG. 7C shows hybridization to CTO and Extension of PTO fragment. FIG. 7D shows cleavage by RNase H and detection. The CTO has a fluorescent single label at its capturing portion. The CTO is immobilized on a solid substrate through its 5'-end.

(FIG. 8A shows hybridization. FIG. 8B shows primer extension and cleavage of PTO. FIG. 8C shows hybridization to CTO and extension of PTO fragment. FIG. 8D shows cleavage by restriction enzyme & detection. The PTO has a fluorescent single label at its tagging portion. The CTO is immobilized on a solid substrate through its 5'-end.

FIG. 9A shows hybridization. FIG. 9B shows primer extension and cleavage of PTO. FIG. 9C shows hybridization to CTO and extension of PTO fragment. FIG. 9D shows cleavage by RNase H and detection. The PTO has a fluorescent single label at its tagging portion. The CTO is immobilized on a solid substrate through its 5'-end.

DETAILED DESCRIPTION OF THIS INVENTION

Figure 1:
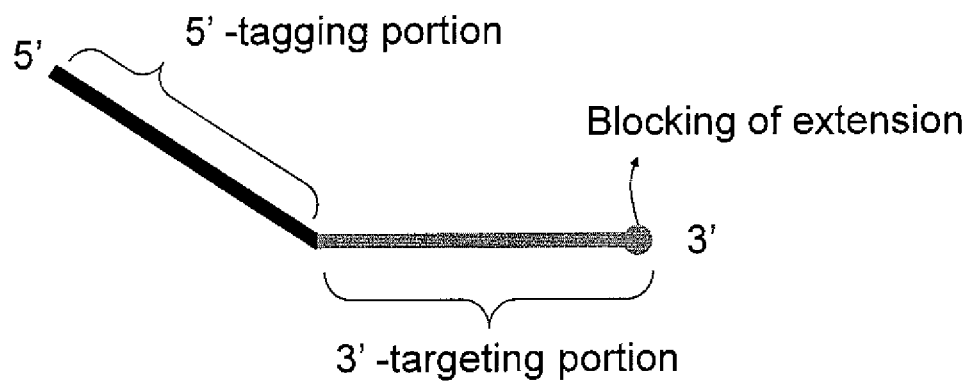
FIG. 1 shows the schematic structures of PTO (Probing and Tagging Oligonucleotide) and CTO (Capturing and Templating Oligonucleotide) used in a PCEC (PTO Cleavage and Extension-Dependent Cleavage) assay. Preferably, the 3'-ends of the PTO and CTO are blocked to prohibit their extension.
Figure 1:
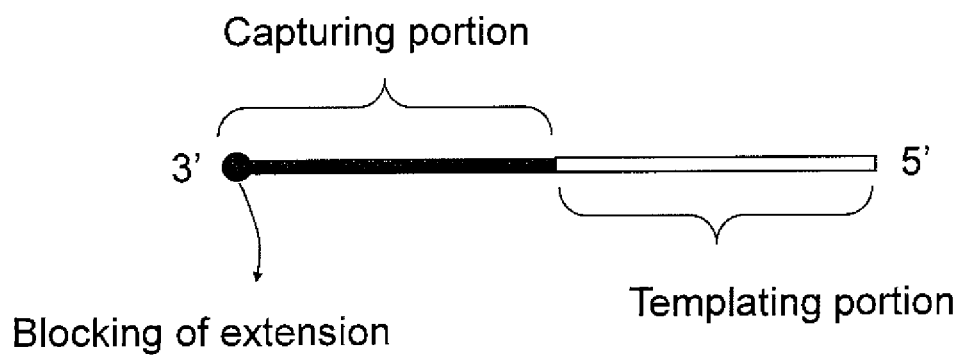

In one aspect of the present invention, there is provided a method for detecting a target nucleic acid sequence from a DNA or a mixture of nucleic acids by a PCEC (PTO Cleavage and Extension-Dependent Cleavage) assay, comprising:

(a) hybridizing the target nucleic acid sequence with an upstream oligonucleotide and a PTO (Probing and Tagging Oligonucleotide); wherein the upstream oligonucleotide comprises a hybridizing nucleotide sequence complementary to the target nucleic acid sequence; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the upstream oligonucleotide is located upstream of the PTO;

(b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO;

(c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and a template-dependent nucleic acid polymerase; wherein the fragment hybridized with the capturing portion of the CTO is extended to form an extended duplex and to generate a cleavage site for a nucleolytic enzyme;

(e) cleaving the extended duplex using the nucleolytic enzyme to form a cleaved fragment; and (f) detecting the occurrence of the cleavage of the extended duplex; whereby the occurrence of the cleavage of the extended duplex indicates the presence of the target nucleic acid sequence.

The present inventors have made intensive researches to develop novel approaches to detect target sequences with more improved accuracy and convenience, inter alia, in a multiplex manner. As a result, we have established novel protocols for detection of target sequences in which target detection is accomplished by not only probe hybridization but also successive cleavage reactions, 5' nucleolytic reaction of the PTO and nucleolytic reaction of the extended duplex. The present protocols are well adopted to liquid phase reactions as well as solid phase reactions, and ensure detection of multiple target sequences with more improved accuracy and convenience.

The present invention employs successive nucleolytic reactions, a first cleavage of the PTO (Probing and Tagging Oligonucleotide) by 5' nucleolytic reaction and a second cleavage of the extended duplex by nucleolytic reaction, thereby generating a target signal. Therefore, it is named as a PCEC (PTO Cleavage and Extension-Dependent Cleavage) assay.

The PCEE assay of the present invention will be described in more detail as follows:

Step (a): Hybridization of an Upstream Oligonucleotide and a PTO with a Target Nucleic Acid Sequence According to the present invention, a target nucleic acid sequence is first hybridized with an upstream oligonucleotide and a PTO (Probing and Tagging Oligonucleotide).

The term used herein "target nucleic acid", "target nucleic acid sequence" or "target sequence" refers to a nucleic acid sequence of interest for detection, which is annealed to or hybridized with a probe or primer under hybridization, annealing or amplifying conditions.

The term used herein "probe" refers to a single-stranded nucleic acid molecule comprising a portion or portions that are substantially complementary to a target nucleic acid sequence.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH.

Preferably, the probe and primer are single-stranded deoxyribonucleotide molecules. The probes or primers used in this invention may be comprised of naturally occurring dNMP (i.e., dAMP, dGM, dCMP and dTMP), modified nucleotide, or non-natural nucleotide. The probes or primers may also include ribonucleotides.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The term used "hybridizing" used herein refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature.

The hybridization of a target nucleic acid sequence with the upstream oligonucleotide and the PTO may be carried out under suitable hybridization conditions routinely determined by optimization procedures. Conditions such as temperature, concentration of components, hybridization and washing times, buffer components, and their pH and ionic strength may be varied depending on various factors, including the length and GC content of oligonucleotide (upstream oligonucleotide and PTO) and the target nucleotide sequence. For instance, when a relatively short oligonucleotide is used, it is preferable that low stringent conditions are adopted. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999).

There is no intended distinction between the terms "annealing" and "hybridizing", and these terms will be used interchangeably.

The upstream oligonucleotide and PTO have hybridizing nucleotide sequences complementary to the target nucleic acid sequence. The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", preferably perfectly complementary.

The 5'-tagging portion of the PTO has a nucleotide sequence non-complementary to the target nucleic acid sequence. The templating portion of the CTO (Capturing and Templating Oligonucleotide) has a nucleotide sequence non-complementary to the 5'-tagging portion and the 3'-targeting portion of the PTO. The term "non-complementary" is used herein to mean that primers or probes are sufficiently non-complementary not to hybridize selectively to a target nucleic acid sequence under the designated annealing conditions or stringent conditions, encompassing the terms "substantially non-complementary" and "perfectly non-complementary", preferably perfectly non-complementary.

The term used herein "PTO (Probing and Tagging Oligonucleotide)" means an oligonucleotide comprising (i) a 3'-targeting portion serving as a probe and (ii) a 5'-tagging portion with a nucleotide sequence non-complementary to the target nucleic acid sequence, which is nucleolytically released from the PTO after hybridization with the target nucleic acid sequence. The 5'-tagging portion and the 3'-targeting portion in the PTO have to be positioned in a 5' to 3' order. The PTO is schematically illustrated in FIG. 1.

Preferably, the hybridization in step (a) is preformed under stringent conditions that the 3'-targeting portion is hybridized with the target nucleic acid sequence and the 5'-tagging portion is not hybridized with the target nucleic acid sequence.

The PTO does not require any specific lengths. For example, the length of the PTO may be 15-150 nucleotides, 15-100 nucleotides, 15-80 nucleotides, 15-60 nucleotides, 15-40 nucleotides, 20-150 nucleotides, 20-100 nucleotides, 20-80 nucleotides, 20-60 nucleotides, 20-50 nucleotides, 30-150 nucleotides, 30-100 nucleotides, 30-80 nucleotides, 30-60 nucleotides, 30-50 nucleotides, 35-100 nucleotides, 35-80 nucleotides, 35-60 nucleotides, or 35-50 nucleotides. The 3'-targeting portion of the PTO may be in any lengths so long as it is specifically hybridized with target nucleic acid sequences. For example, the 3'-targeting portion of the PTO may be 10-100 nucleotides, 10-80 nucleotides, 10-50 nucleotides, 10-40 nucleotides, 10-30 nucleotides, 15-100 nucleotides, 15-80 nucleotides, 15-50 nucleotides, 15-40 nucleotides, 15-30 nucleotides, 20-100 nucleotides, 20-80 nucleotides, 20-50 nucleotides, 20-40 nucleotides or 20-30 nucleotides in length. The 5'-tagging portion may be in any lengths so long as it is specifically hybridized with the templating portion of the CTO and then extended. For instance, the 5'-tagging portion of the PTO may be 5-50 nucleotides, 5-40 nucleotides, 5-30 nucleotides, 5-20 nucleotides, 10-50 nucleotides, 10-40 nucleotides, 10-30 nucleotides, 10-20 nucleotides, 15-50 nucleotides, 15-40 nucleotides, 15-30 nucleotides or 15-20 nucleotides in length.

The 3'-end of the PTO may have a 3'-OH terminal. Preferably, the 3'-end of the PTO is "blocked" to prohibit its extension.

The blocking may be achieved in accordance with conventional methods. For instance, the blocking may be performed by adding to the 3'-hydroxyl group of the last nucleotide a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

Alternatively, the PTO may be designed to have a hairpin structure.

The non-hybridization between the 5'-tagging portion of the PTO and the target nucleic acid sequence refers to non-formation of a stable double-strand between them under certain hybridization conditions. According to a preferred embodiment, the 5'-tagging portion of the PTO not involved in the hybridization with the target nucleic acid sequence forms a single-strand.

The upstream oligonucleotide is located upstream of the PTO.

In addition, the upstream oligonucleotide or its extended strand hybridized with the target nucleic acid sequence induces cleavage of the PTO by an enzyme having a 5' nuclease activity.

The induction of the PTO cleavage by the upstream oligonucleotide may be accomplished by two fashions: (i) upstream oligonucleotide extension-independent cleavage induction; and (ii) upstream oligonucleotide extension-dependent cleavage induction.

Where the upstream oligonucleotide is positioned adjacently to the PTO sufficient to induce the PTO cleavage by an enzyme having a 5' nuclease activity, the enzyme bound to the upstream oligonucleotide digests the PTO with no extension reaction. In contrast, where the upstream oligonucleotide is positioned distantly to the PTO, an enzyme having a polymerase activity (e.g., template-dependent polymerase) catalyzes extension of the upstream oligonucleotide (e.g., upstream primer) and an enzyme having a 5' nuclease activity bound to the extended product digests the PTO.

Therefore, the upstream oligonucleotide may be located relatively to the PTO in two fashions. The upstream oligonucleotide may be located adjacently to the PTO sufficient to induce the PTO cleavage in an extension-independent manner. Alternatively, the upstream oligonucleotide may be located distantly to the PTO sufficient to induce the PTO cleavage in an extension-dependent manner.

The term used herein "adjacent" with referring to positions or locations means that the upstream oligonucleotide is located adjacently to the 3'-targeting portion of the PTO to form a nick. Also, the term means that the upstream oligonucleotide is located 1-30 nucleotides, 1-20 nucleotides or 1-15 nucleotides apart from the 3'-targeting portion of the PTO.

The term used herein "distant" with referring to positions or locations includes any positions or locations sufficient to ensure extension reactions.

According to a preferred embodiment, the upstream oligonucleotide is located distantly to the PTO sufficient to induce the PTO cleavage in an extension-dependent manner.

According to a preferred embodiment, the upstream oligonucleotide is an upstream primer or an upstream probe. The upstream primer is suitable in an extension-independent cleavage induction or an extension-dependent cleavage, and the upstream probe is suitable in an extension-independent cleavage induction.

Alternatively, the upstream oligonucleotide may have a partial-overlapped sequence with the 5'-part of the 3'-targeting portion of the PTO. Preferably, the overlapped sequence is 1-10 nucleotides, more preferably 1-5 nucleotides, still more preferably 1-3 nucleotides in length. Where the upstream oligonucleotide has a partial-overlapped sequence with the 5'-part of the 3'-targeting portion of the PTO, the 3'-targeting portion is partially digested along with the 5'-tagging portion in the cleavage reaction of the step (b). In addition, the overlapped sequence permits to cleave a desired site of the 3'-targeting portion.

According to a preferred embodiment, the upstream primer induces through its extended strand the cleavage of the PTO by the enzyme having the 5' nuclease activity.

The conventional technologies for cleavage reactions by upstream oligonucleotides may be applied to the present invention, so long as the upstream oligonucleotide induces cleavage of the PTO hybridized with the target nucleic acid sequence to release a fragment comprising the 5'-tagging portion or a part of the 5'-tagging portion of the PTO. For example, U.S. Pat. Nos. 5,210,015, 5,487,972, 5,691,142, 5,994,069 and 7,381,532 and U.S. Appln. Pub. No. 2008-0241838 may be applied to the present invention.

According to a preferred embodiment, the method is performed in the presence of a downstream primer. The downstream primer generates additionally a target nucleic acid sequence to be hybridized with the PTO, enhancing sensitivity in a target detection.

According to a preferred embodiment, when the upstream primer and the downstream primer are used, a template-dependent nucleic acid polymerase is additionally employed for extension of the primers.

According to a preferred embodiment, the upstream oligonucleotide (upstream primer or upstream probe), the downstream primer and/or 5'-tagging portion of the PTO have a dual priming oligonucleotide (DPO) structure developed by the present inventor. The oligonucleotides having the DPO structure show significantly improved target specificity compared with conventional primers and probes (see WO 2006/095981; Chun et al., Dual priming oligonucleotide system for the multiplex detection of respiratory viruses and SNP genotyping of CYP2C19 gene, *Nucleic Acid Research*, 35:6e40 (2007)).

According to a preferred embodiment, the 3'-targeting portion of the PTO has a modified dual specificity oligonucleotide (mDSO) structure developed by the present inventor. The modified dual specificity oligonucleotide (mDSO) structure shows significantly improved target specificity compared with conventional probes (see WO 2011/028041)

Step (b): Release of a Fragment from the PTO

Afterwards, the resultant of the step (a) is contacted to an enzyme having a 5' nuclease activity under conditions for cleavage of the PTO. The PTO hybridized with the target nucleic acid sequence is digested by the enzyme having the 5' nuclease activity to release a fragment comprising the 5'-tagging portion or a part of the 5'-tagging portion of the PTO.

The term used herein "conditions for cleavage of the PTO" means conditions sufficient to digest the PTO hybridized with the target nucleic acid sequence by the enzyme having the 5' nuclease activity, such as temperature, pH, ionic strength, buffer, length and sequence of oligonucleotides and enzymes. For example, when Taq DNA polymerase is used as the enzyme having the 5' nuclease activity, the conditions for cleavage of the PTO include Tris-HCl buffer, KCl, $MgCl_2$ and temperature.

Figure 2:
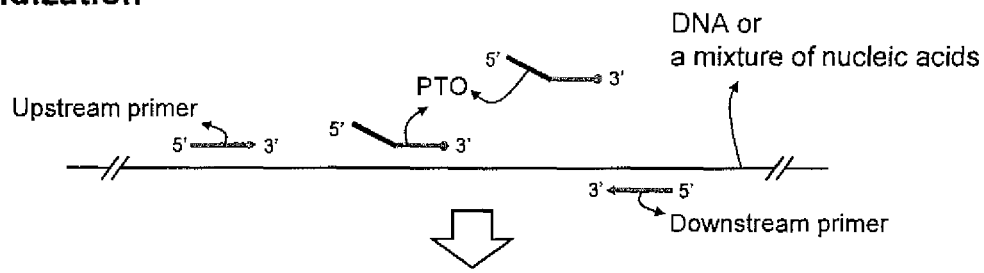
FIG. 2 represents schematically an embodiment of a PCEC assay using a cleavage site for 5' to 3' exonuclease.
Figure 2:
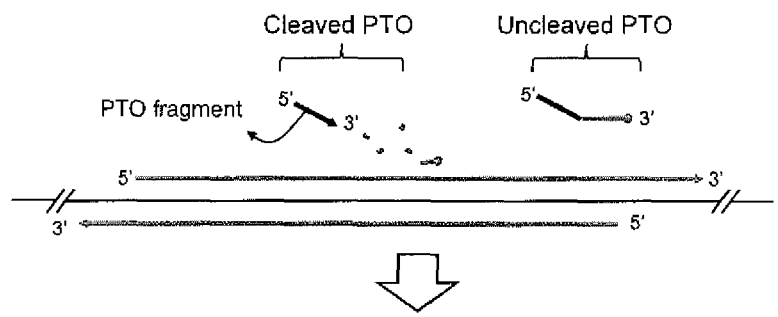
Figure 2:
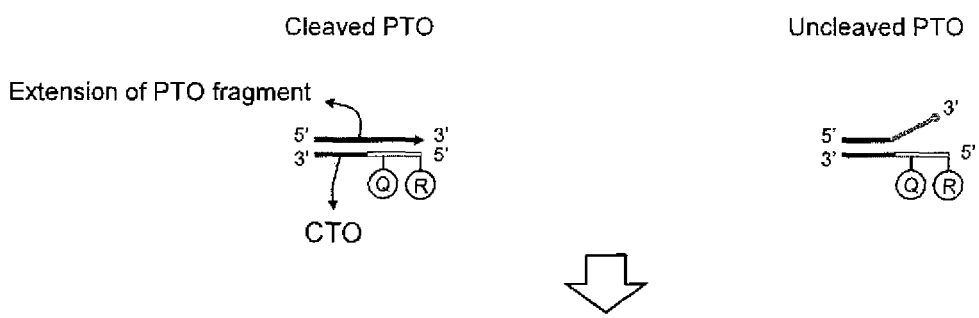
Figure 2:

When the PTO is hybridized with the target nucleic acid sequence, its 3'-targeting portion is involved in the hybridization and the 5'-tagging portion forms a single-strand with no hybridization with the target nucleic acid sequence (see FIG. 2). As such, an oligonucleotide comprising both single-stranded and double-stranded structures may be digested using an enzyme having a 5' nuclease activity by a variety of technologies known to one of skill in the art.

The cleavage sites of the PTO are varied depending on the type of upstream oligonucleotides (upstream probe or upstream primer), hybridization sites of upstream oligonucleotides and cleavage conditions (see U.S. Pat. Nos. 5,210,015, 5,487,972, 5,691,142, 5,994,069 and 7,381,532 and U.S. Appln. Pub. No. 2008-0241838).

A multitude of conventional technologies may be employed for the cleavage reaction of the PTO, releasing a fragment comprising the 5'-tagging portion or a part of the 5'-tagging portion.

Briefly, there may be three sites of cleavage in the step (b). Firstly, the cleavage site is a junction site between a hybridization portion of the PTO (3'-targeting portion) and a non-hybridization portion (5'-tagging portion). The second cleavage site is a site located several nucleotides in a 3'-direction apart from the 3'-end of the 5'-tagging portion of the PTO. The second cleavage site is located at the 5'-end part of the 3'-targeting portion of the PTO. The third cleavage site is a site located several nucleotides in a 5'-direction apart from the 3'-end of the 5'-tagging portion of the PTO.

According to a preferred embodiment, the initial site for the cleavage of the PTO by the template-dependent polymerase having the 5' nuclease activity upon extension of the upstream primer is a starting point of the double strand between the PTO and the target nucleic acid sequence or a site 1-3 nucleotides apart from the starting point.

In this regard, the term used herein "a fragment comprising the 5'-tagging portion or a part of the 5'-tagging portion of the PTO" in conjunction with cleavage of the PTO by the enzyme having the 5' nuclease activity is used to encompass (i) the 5'-tagging portion, (ii) the 5'-tagging portion and the 5'-end part of the 3'-targeting portion and (iii) a part of the 5'-tagging portion. In this application, the term "a fragment comprising the 5'-tagging portion or a part of the 5'-tagging portion of the PTO" may be also described as "PTO fragment".

The term "part" used in conjunction with the PTO or CTO such as the part of the 5'-tagging portion of the PTO, the 5'-end part of the 3'-targeting portion of the PTO and the 5'-end part of the capturing portion of the CTO refers to a nucleotide sequence composed of 1-40, 1-30, 1-20, 1-15, 1-10 or 1-5 nucleotides, preferably 1, 2, 3 or 4 nucleotides.

According to a preferred embodiment, the enzyme having the 5' nuclease activity is DNA polymerase having a 5' nuclease activity or FEN nuclease, more preferably a thermostable DNA polymerase having a 5' nuclease activity or FEN nuclease.

A suitable DNA polymerase having a 5' nuclease activity in this invention is a thermostable DNA polymerase obtained from a variety of bacterial species, including *Thermus aquaticus* (Taq), *Thermus thermophilus* (Tth), *Thermus filiformis*, *Thermis flavus*, *Thermococcus literalis*, *Thermus antranikianii*, *Thermus caldophilus*, *Thermus chliarophilus*, *Thermus flavus*, *Thermus igniterrae*, *Thermus lacteus*, *Thermus oshimai*, *Thermus ruber*, *Thermus rubens*, *Thermus scotoductus*, *Thermus silvanus*, *Thermus* species Z05, *Thermus* species sps 17, *Thermus thermophilus*, *Thermotoga martima*, *Thermotoga neapolitana*, *Thermosipho africanus*, *Thermococcus litoralis*; *Thermococcus barossi*, *Thermococcus gorgonarius*, *Thermotoga maritima*, *Thermotoga neapolitana*, *Thermosiphoafricanus*, *Pyrococcus woesei*, *Pyrococcus horikoshii*, *Pyrococcus abyssi*, *Pyrodictium occultum*, *Aquifex pyrophilus* and *Aquifex aeolieus*. Most preferably, the thermostable DNA polymerase is Taq polymerase.

Alternatively, the present invention may employ DNA polymerases having a 5' nuclease activity modified to have less polymerase activities.

The FEN (flap endonuclease) nuclease used is a 5' flap-specific nuclease.

The FEN nuclease suitable in the present invention comprises FEN nucleases obtained from a variety of bacterial species, including *Sulfolobus solfataricus*, *Pyrobaculum aerophilum*, *Thermococcus litoralis*; *Archaeaglobus veneficus*, *Archaeaglobus profundus*, *Acidianus brierlyi*, *Acidianus ambivalens*, *Desulfurococcus amylolyticus*, *Desulfurococcus mobilis*, *Pyrodictium brockii*, *Thermococcus gorgonarius*, *Thermococcus zilligii*, *Methanopyrus kandleri*, *Methanococcus igneus*, *Pyrococcus horikoshii*, *Aeropyrum pernix*, and *Archaeaglobus veneficus*.

Where the upstream primer is used in the step (a), it is preferable that the conditions for cleavage of the PTO comprise extension reaction of the upstream primer.

According to a preferred embodiment, the upstream primer is used in the step (a), a template-dependent polymerase is used for extension of the upstream primer and the template-dependent polymerase is identical to the enzyme having the 5' nuclease activity.

Optionally, the upstream primer is used in the step (a), a template-dependent polymerase is used for extension of the upstream primer and the template-dependent polymerase is different from the enzyme having the 5' nuclease activity.

Alternatively, the present invention may be carried out with no use of the upstream oligonucleotide. The PTO may be cleaved by upstream oligonucleotide-independent 5' nuclease activity. In such case, conventional enzymes having upstream oligonucleotide-independent 5' nuclease activity may be used. Among template-dependent polymerases having 5' nuclease activity, there are several enzymes having upstream oligonucleotide-independent 5' nuclease activity, e.g., Taq DNA polymerase.

Considering amplification of target nucleic acid sequences and cleavage efficiency of the PTO, the PCEC assay of the present invention is preferably performed using upstream oligonucleotides.

Step (c): Hybridization of the Fragment Released from the PTO with CTO

The fragment released from the PTO is hybridized with a CTO (Capturing and Templating Oligonucleotide).

The CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO.

The CTO is acted as a template for extension of the fragment released from the PTO. The fragment serving as a primer is hybridized with the CTO and extended to form an extended duplex.

The templating portion may comprise any sequence so long as it is non-complementary to the 5'-tagging portion and the 3'-targeting portion of the PTO. Furthermore, the templating portion may comprise any sequence so long as it can be acted as a template for extension of the fragment released from the PTO.

As described above, when the fragment having the 5'-tagging portion of the PTO is released, it is preferred that the capturing portion of the CTO is designed to comprise a nucleotide sequence complementary to the 5'-tagging portion. When the fragment having the 5'-tagging portion and a 5'-end part of the 3'-targeting portion is released, it is preferred that the capturing portion of the CTO is designed to comprise a nucleotide sequence complementary to the 5'-tagging portion and the 5'-end part of the 3'-targeting portion. When the fragment having a part of the 5'-tagging portion of the PTO is released, it is preferred that the capturing portion of the CTO is designed to comprise a nucleotide sequence complementary to the part of the 5'-tagging portion.

Moreover, it is possible to design the capturing portion of the CTO with anticipating cleavage sites of the PTO. For example, where the capturing portion of the CTO is designed to comprise a nucleotide sequence complementary to the 5'-tagging portion, either the fragment having a part of the 5'-tagging portion or the fragment having the 5'-tagging portion can be hybridized with the capturing portion and then extended. Where the fragment comprising the 5'-tagging portion and a 5'-end part of the 3'-targeting portion is released, it may be hybridized with the capturing portion of the CTO designed to comprise a nucleotide sequence complementary to the 5'-tagging portion and then successfully extended although mismatch nucleotides are present at the 3'-end portion of the fragment. That is because primers can be extended depending on reaction conditions although its 3'-end contains some mismatch nucleotides (e.g. 1-3 mismatch nucleotides).

When the fragment comprising the 5'-tagging portion and a 5'-end part of the 3'-targeting portion is released, the 5'-end part of the capturing portion of the CTO may be designed to have a nucleotide sequence complementary to the cleaved 5'-end part of the 3'-targeting portion, overcoming problems associated with mismatch nucleotides (see FIG. 1).

Preferably, the nucleotide sequence of the 5'-end part of the capturing portion of the CTO complementary to the cleaved 5'-end part of the 3'-targeting portion may be selected depending on anticipated cleavage sites on the 3'-targeting portion of the PTO. It is preferable that the nucleotide sequence of the 5'-end part of the capturing portion of the CTO complementary to the cleaved 5'-end part of the 3'-targeting portion is 1-10 nucleotides, more preferably 1-5 nucleotides, still more preferably 1-3 nucleotides.

The 3'-end of the CTO may comprise additional nucleotides not involved in hybridization with the fragment. Moreover, the capturing portion of the CTO may comprise a nucleotide sequence complementary only to a part of the fragment (e.g., a part of the fragment containing its 3'-end portion) so long as it is stably hybridized with the fragment.

The term used "capturing portion comprising a nucleotide sequence complementary to the 5'-tagging portion or a part of the 5'-tagging portion" is described herein to encompass various designs and compositions of the capturing portion of the CTO as discussed above.

The CTO may be designed to have a hairpin structure.

The length of the CTO may be widely varied. For example, the CTO is 7-1000 nucleotides, 7-500 nucleotides, 7-300 nucleotides, 7-100 nucleotides, 7-80 nucleotides, 7-60 nucleotides, 7-40 nucleotides, 15-1000 nucleotides, 15-500 nucleotides, 15-300 nucleotides, 15-100 nucleotides, 15-80 nucleotides, 15-60 nucleotides, 15-40 nucleotides, 20-1000 nucleotides, 20-500 nucleotides, 20-300 nucleotides, 20-100 nucleotides, 20-80 nucleotides, 20-60 nucleotides, 20-40 nucleotides, 30-1000 nucleotides, 30-500 nucleotides, 30-300 nucleotides, 30-100 nucleotides, 30-80 nucleotides, 30-60 nucleotides or 30-40 nucleotides in length. The capturing portion of the CTO may have any length so long as it is specifically hybridized with the fragment released from the PTO. For example, the capturing portion of the CTO is 5-100 nucleotides, 5-60 nucleotides, 5-40 nucleotides, 5-30 nucleotides, 5-20 nucleotides, 10-100 nucleotides, 10-60 nucleotides, 10-40 nucleotides, 10-30 nucleotides, 10-20 nucleotides, 15-100 nucleotides, 15-60 nucleotides, 15-40 nucleotides, 15-30 nucleotides or 15-20 nucleotides in length. The templating portion of the CTO may have any length so long as it can act as a template in extension of the fragment released from the PTO. For example, the templating portion of the CTO is 1-900 nucleotides, 1-400 nucleotides, 1-300 nucleotides, 1-100 nucleotides, 1-80 nucleotides, 1-60 nucleotides, 1-40 nucleotides, 1-20 nucleotides, 2-900 nucleotides, 2-400 nucleotides, 2-300 nucleotides, 2-100 nucleotides, 2-80 nucleotides, 2-60 nucleotides, 2-40 nucleotides, 2-20 nucleotides, 5-900 nucleotides, 5-400 nucleotides, 5-300 nucleotides, 5-100 nucleotides, 5-80 nucleotides, 5-60 nucleotides, 5-40 nucleotides, 5-30 nucleotides, 10-900 nucleotides, 10-400 nucleotides, 10-300 nucleotides, 15-900 nucleotides, 15-100 nucleotides, 15-80 nucleotides, 15-60 nucleotides, 15-40 nucleotides or 15-20 nucleotides in length.

The 3'-end of the CTO may have a 3'-OH terminal. Preferably, the 3'-end of the CTO is blocked to prohibit its extension. The non-extendible blocking of the CTO may be achieved in accordance with conventional methods. For instance, the blocking may be performed by adding to the 3'-hydroxyl group of the last nucleotide of the CTO a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

The fragment released from the PTO is hybridized with the CTO, providing a form suitable in extension of the fragment. Although an undigested PTO is also hybridized with the capturing portion of the CTO through its 5'-tagging portion, its 3'-targeting portion is not hybridized to the CTO which prohibits the formation of an extended duplex.

The hybridization in the step (c) can be described in detail with referring to descriptions in the step (a).

Step (d): Extension of the PTO Fragment and Generation of Cleavage Site for Nucleolytic Enzyme The extension reaction is carried out using the resultant of the step (c) and a template-dependent nucleic acid polymerase. The PTO fragment hybridized with the capturing portion of the CTO is extended to form an extended duplex and to generate a cleavage site for a nucleolytic enzyme. In contrast, uncleaved PTO hybridized with the capturing portion of the CTO is not extended such that no cleavage site for a nucleolytic enzyme is generated.

The term used herein "extended duplex" means a duplex formed by extension reaction in which the fragment hybridized with the capturing portion of the CTO is extended using the templating portion of the CTO as a template and the template-dependent nucleic acid polymerase.

Upon the formation of the extended duplex, the cleavage site for nucleolytic enzymes is generated. A multitude of nucleolytic enzymes acting specifically on a duplex structure have been known to one of skill in the art. Nucleolytic enzymes in the present invention provides signal indicative of the presence of the target nucleic acid sequence.

According to a preferred embodiment, the nucleolytic enzyme is a restriction enzyme, the templating portion of the CTO comprises a sequence recognized by the restriction enzyme and the formation of the extended duplex in the step (d) generates a cleavage site of the restriction enzyme. The extended duplex with the newly-introduced cleavage site is then cleaved by restriction enzymes to a cleaved fragment indicating the presence of the target nucleic acid sequence.

According to a preferred embodiment, the nucleolytic enzyme is a ribonuclease, the templating portion of the CTO comprises a RNA sequence and the formation of the extended duplex in the step (d) produces the DNA-RNA hybrid duplex to generate a cleavage site of the ribonuclease.

According to a preferred embodiment, the nucleolytic enzyme is a 5' to 3' exonuclease and the formation of the extended duplex in the step (d) generates on the CTO a cleavage site of the 5' to 3' exonuclease. The newly-introduced cleavage site on the CTO is newly generated only after the formation of the extended duplex and cleaved by 5' to 3' exonucleases to a cleaved fragment containing the 5'-end of the CTO which indicates the presence of the target nucleic acid sequence.

According to a preferred embodiment, the cleavage site for the nucleolytic enzyme generated by the formation of the extended duplex is a cleavage site for a nucleolytic enzyme capable of cleaving a DNA duplex, a RNA duplex or a DNA-RNA hybrid duplex.

The PTO and/or the CTO may be designed and constructed such that a desired type of cleavage sites for nucleolytic enzymes is introduced.

Where cleavage sites for nucleolytic enzymes acting on a DNA duplex (e.g., restriction enzymes and 5' to 3' exonucleases) is intended to generate, the PTO and the CTO each composed of DNA molecules are preferably used. The PTO fragment composed of DNA molecules is extended using dNTPs to form the extended duplex, thereby generating a cleavage site for nucleolytic enzymes acting on a DNA duplex (e.g., restriction enzymes and 5' to 3' exonucleases).

Where cleavage sites for nucleolytic enzymes acting on a RNA duplex are intended to generate, the PTO composed of RNA molecules or the PTO of which 5'-tagging portion is composed of RNA molecules, and the CTO composed of RNA molecules are preferably used. The PTO fragment composed of RNA molecules hybridized with the CTO composed of RNA molecules is extended using NTPs to form the extended duplex, thereby generating a cleavage site for nucleolytic enzymes acting on a RNA duplex.

Where cleavage sites for nucleolytic enzymes acting on a DNA-RNA hybrid duplex are intended to generate, the PTO composed of DNA molecules and the CTO of which templating portion is composed of RNA molecules are preferably used. The RNA molecule of the templating portion comprises 1-10 ribonucleotides. The PTO fragment composed of DNA molecules hybridized with the CTO of which templating portion is composed of RNA molecules is extended using dNTPs to form the extended duplex, thereby generating a cleavage site for nucleolytic enzymes (e.g., RNase H) acting on a DNA-RNA hybrid duplex.

The template-dependent nucleic acid polymerase used in the step (d) for the extension reaction may include any nucleic acid polymerases, for example, Klenow fragment of *E. coli* DNA polymerase I, a thermostable DNA polymerase and bacteriophage T7 DNA polymerase. Preferably, the polymerase is a thermostable DNA polymerase which may be obtained from a variety of bacterial species, including *Thermus aquaticus* (Taq), *Thermus thermophilus* (Tth), *Thermus filiformis, Thermis flavus, Thermococcus literalis, Thermus antranikianii, Thermus caldophilus, Thermus chliarophilus, Thermus flavus, Thermus igniterrae, Thermus lacteus, Thermus oshimai, Thermus ruber, Thermus rubens, Thermus scotoductus, Thermus silvanus, Thermus* species Z05, *Thermus* species sps 17 *Thermus thermophilus, Thermotoga maritima, Thermotoga neapolitana, Thermosipho africanus, Thermococcus litoralis, Thermococcus barossi, Thermococcus gorgonarius, Thermotoga maritima, Thermotoga neapolitana, Thermosiphoafricanus, Pyrococcus furiosus* (Pfu), *Pyrococcus woesei, Pyrococcus horikoshii, Pyrococcus abyssi, Pyrodictium occultum, Aquifex pyrophilus* and *Aquifex aeolieus*. Most preferably, the template-dependent nucleic acid polymerase is Taq polymerase.

According to a preferred embodiment, the enzyme having the 5' nuclease activity used in the step (b) is identical to the template-dependent nucleic acid polymerase used in the step (d). More preferably, the enzyme having the 5' nuclease activity used in the step (b), the template-dependent nucleic acid polymerase used for extension of the upstream primer and the template-dependent nucleic acid polymerase used in the step (d) for the extension reaction are identical to one another.

Step (e): Cleavage of the Extended Duplex Using Nucleolytic Enzymes

Following the generation of a cleavage site for a nucleolytic enzyme by the formation of the extended duplex, the extended duplex is cleaved by a suitable nucleolytic enzyme to form a cleaved fragment.

According to a preferred embodiment, the cleaved fragment of the extended duplex may be in a single strand or double strand and the cleavage of the extended duplex may form at least two fragments. For example, the cleavage of the extended duplex by restriction enzymes forms two cleaved fragments in a double stand and the double-stranded fragments may be dissociated to a single stand form depending on reaction conditions. In the cleavage reaction using 5' to 3' exonucleases, a single cleaved fragment may be formed.

In the present application, the cleavage reaction in the step (b) is referred to as a first cleavage reaction and the cleavage reaction in the step (e) to as a second cleavage reaction.

Nucleolytic enzymes used in the second cleavage reaction include any enzymes known to one of skill in the art.

According to a preferred embodiment, the nucleolytic enzyme used in the second cleavage reaction includes a 5' to 3' exonuclease, a restriction enzyme and a ribonuclease, more preferably a thermostable 5' to 3' exonuclease, restriction enzyme and ribonuclease.

According to a preferred embodiment, the nucleolytic enzyme used in the second cleavage reaction includes a nucleolytic enzyme acting specifically on a duplex molecule.

Figure 5:
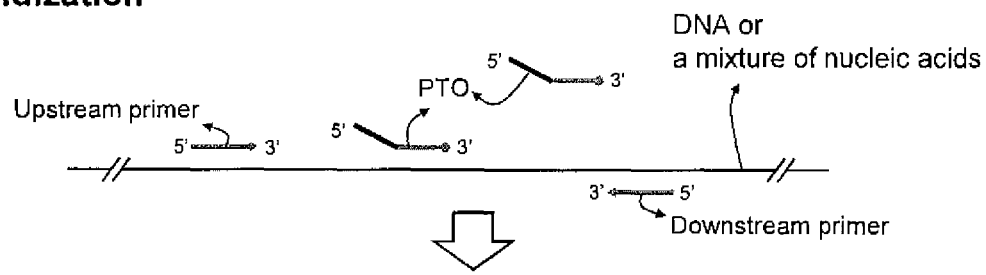
FIG. 5 represents schematically an embodiment of a PCEC assay using a cleavage site for 5' to 3' exonuclease.
Figure 5:
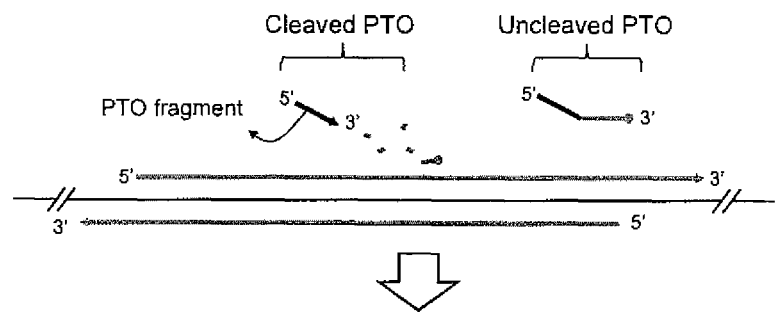
Figure 5:
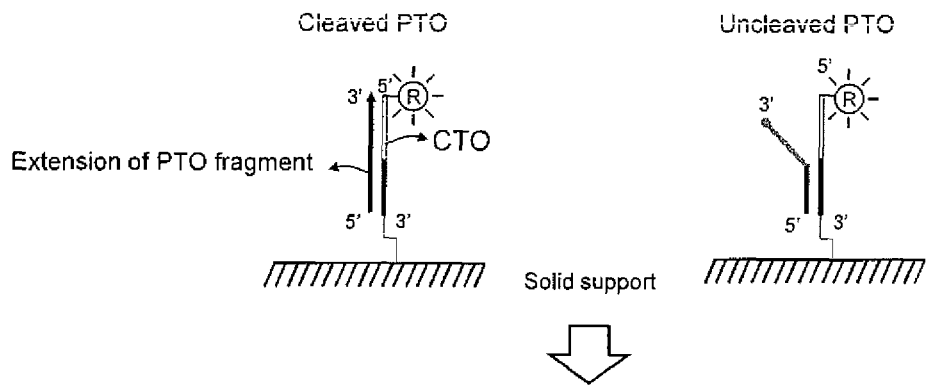
Figure 5:
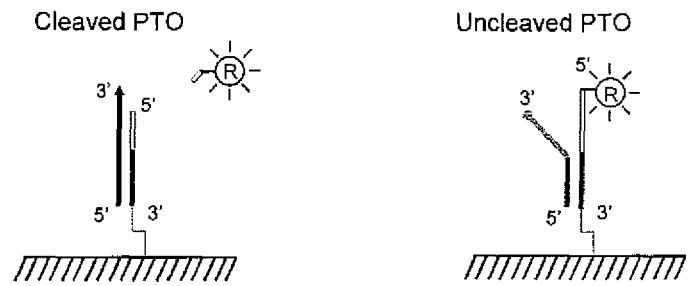

Of nucleolytic enzymes, the 5' to 3' exonuclease cleaves the 5'-end of a DNA duplex. As represented in FIGS. 2 and 5, the PTO fragment formed by cleavage of the PTO hybridized with the target nucleic acid sequence is hybridized with the CTO and then extended to form the extended duplex. The 5'-end of the CTO in the extended duplex is cleaved by the 5' to 3' exonuclease to form the cleaved fragment indicating the presence of the target nucleic acid sequence.

Template-dependent DNA polymerases having a 5' nuclease activity have a 5' to 3' exonuclease activity and in some polymerases, even a 5' to 3' endonuclease activity.

Template-dependent DNA polymerases having a 5' nuclease activity may induce upstream oligonucleotide-dependent cleavage reaction as the step (b) (see, U.S. Pat. No. 5,210,015). In addition, they may also induce upstream oligonucleotide-independent cleavage reaction (see, lawyer et al, *Genome Res.* 1993, 2:275-287 and WO 2008/011004).

According to a preferred embodiment, the 5' to 3' exonuclease is a template-dependent DNA polymerase having a 5' to 3' exonuclease activity, more preferably a thermostable DNA polymerase. The thermostable DNA polymerase can be described in detail with referring to descriptions in the step (b). Preferably, the 5' to 3' exonuclease for cleavage of the extended duplex is Taq polymerase.

According to a preferred embodiment, the template-dependent DNA polymerase having a 5' nuclease activity may induce upstream oligonucleotide-independent cleavage reaction to digest the extended duplex in the step (e).

According to a preferred embodiment, the template-dependent DNA polymerase having a 5' nuclease activity induces not only upstream oligonucleotide-dependent cleavage in the step (b) but also upstream oligonucleotide-independent cleavage of the extended duplex in the step (e).

According to a preferred embodiment, the upstream oligonucleotide-independent cleavage of the extended duplex by a 5' to 3' exonuclease activity of the template-dependent DNA polymerase exhibits an efficiency to generate signals showing the occurrence of the cleavage of the extended duplex.

According to a preferred embodiment, the cleavage of the extended duplex by the template-dependent DNA polymerase having an upstream oligonucleotide-independent 5' nuclease activity is affected by position of labels or linking type of labels present in the extended duplex. Preferably, where a label is linked to the 5'-end of the CTO in the extended duplex, the cleavage of the extended duplex by the template-dependent DNA polymerase having a 5' nuclease activity may be more efficient if the label is linked to a phosphate group of the 5'-end of the CTO, particularly through a carbon-spacer. Where the label is linked to a base of the 5'-end of the CTO or the carbon-spacer is not used, the cleavage of the extended duplex is unlikely to occur.

Where the 5' to 3' exonuclease is used as nucleolytic enzymes, it is preferred that a label for detection of the occurrence of cleavage of the extended duplex is not linked to the PTO.

Figure 3:
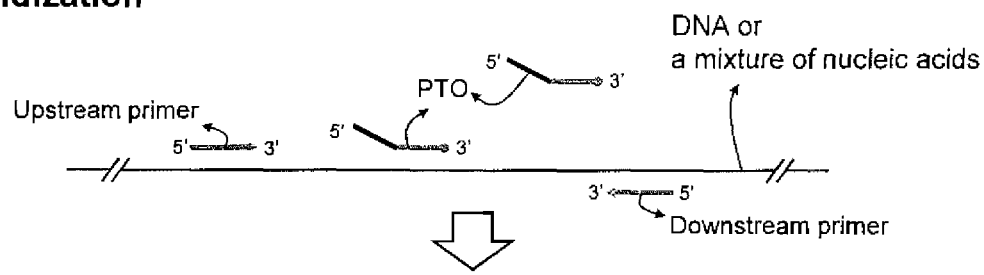
FIG. 3 represents schematically an embodiment of a PCEC assay using a cleavage site for restriction enzyme.
Figure 3:
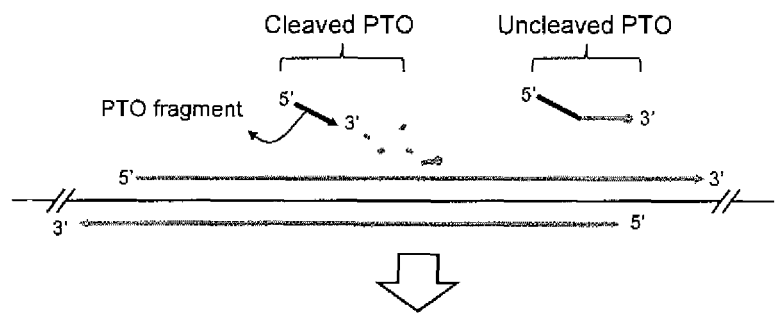
Figure 3:
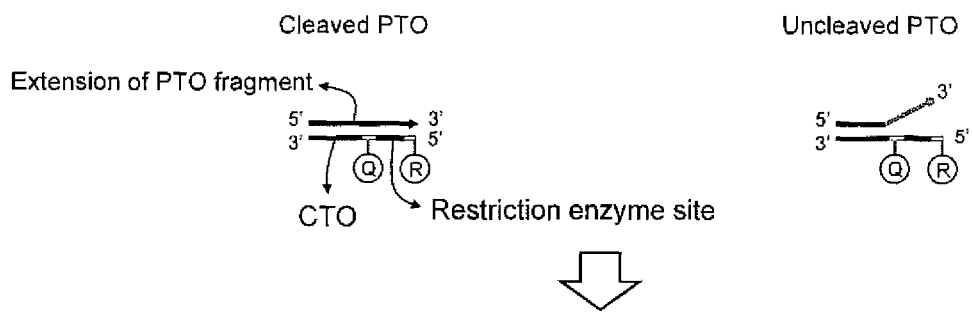
Figure 3:
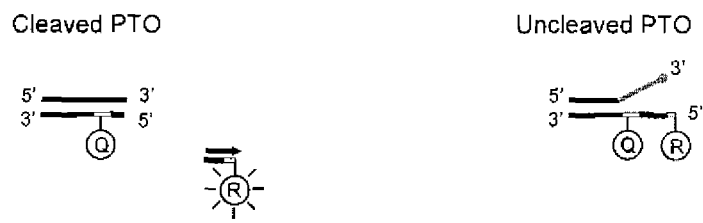
Figure 6:
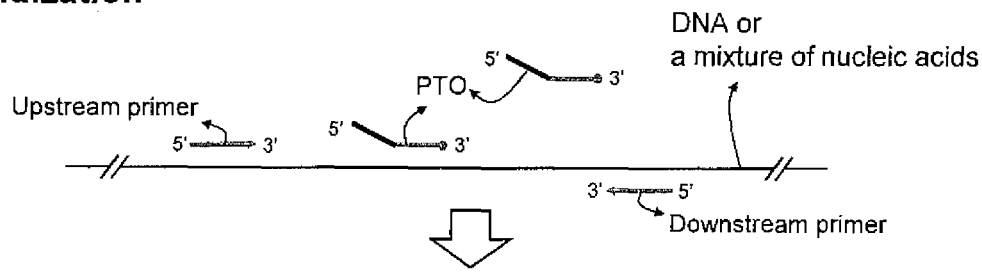
FIG. 6 represents schematically an embodiment of a PCEC assay using a cleavage site for restriction enzyme.
Figure 6:
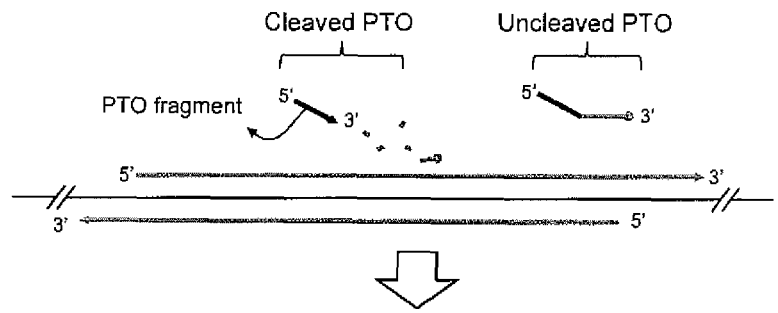
Figure 6:
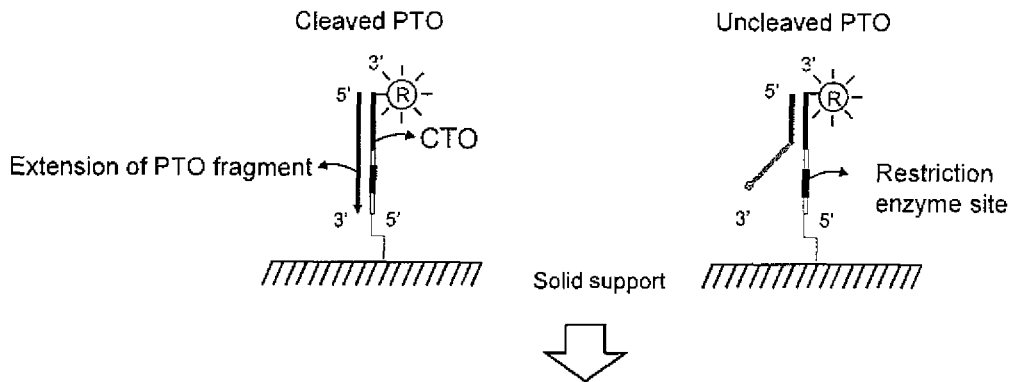
Figure 6:
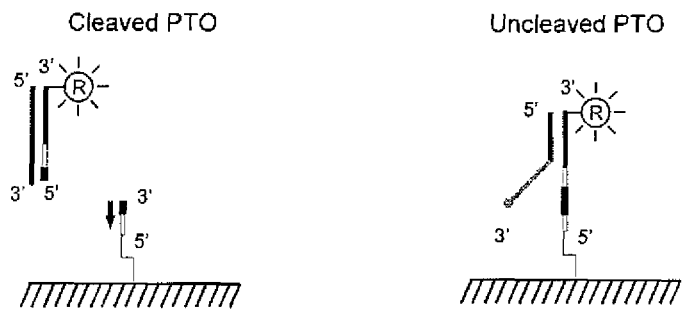
Figure 8:
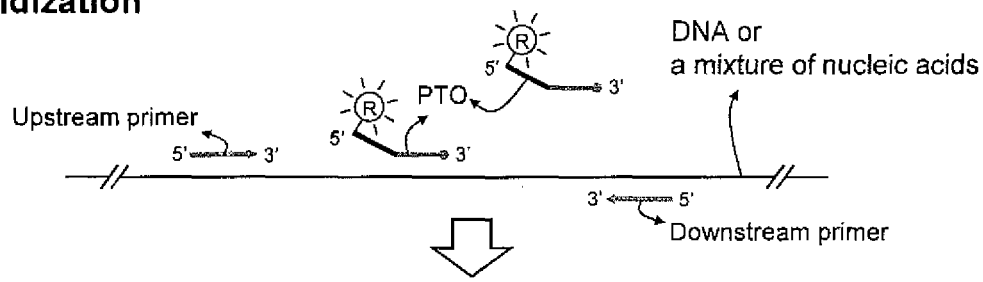
FIG. 8 represents schematically an embodiment of a PCEC assay using a cleavage site for restriction enzyme.
Figure 8:
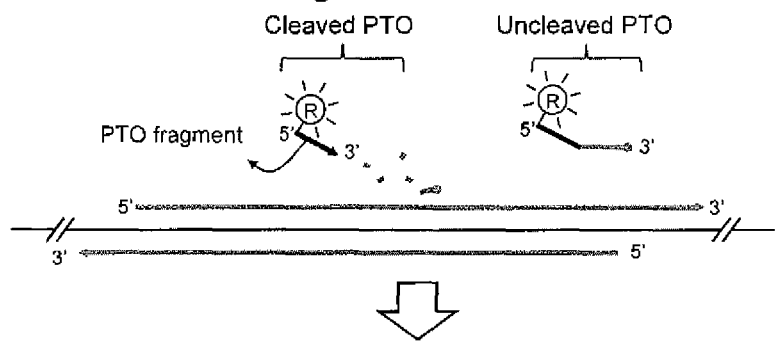
Figure 8:
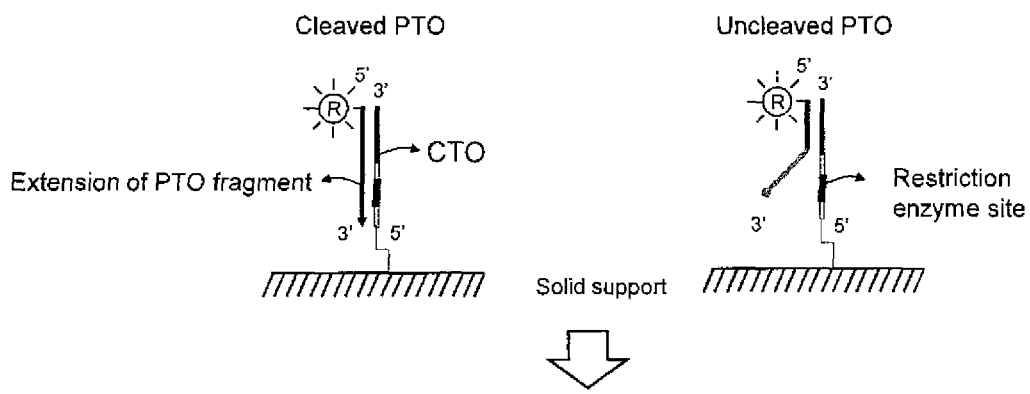
Figure 8:
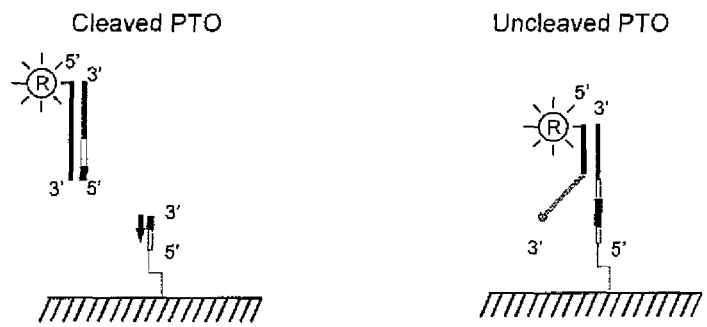

Among nucleolytic enzymes, the restriction enzyme cleaves a cleavage site for restriction enzymes generated by the formation of the extended duplex in the step (d). As represented in FIGS. 3, 6 and 8, the PTO fragment formed by cleavage of the PTO hybridized with the target nucleic acid sequence is hybridized with the CTO (comprising a sequence recognized by the restriction enzyme) and then extended to form the extended duplex having a cleavage site for the restriction enzyme. The restriction enzyme endonucleolytically cleaves the extended duplex to form the cleaved fragment indicating the presence of the target nucleic acid sequence.

According to a preferred embodiment, the restriction enzyme is a restriction enzyme specifically recognizing and digesting a specific sequence of a duplex, more preferably a thermostable restriction enzyme. Various restriction enzymes known in the art may be used.

According to a preferred embodiment, the nucleolytic enzyme is a ribonuclease, the templating portion of the CTO comprises a RNA sequence and the formation of the extended duplex in the step (d) produces the DNA-RNA hybrid duplex to generate a cleavage site of the ribonuclease. The cleavage site of the ribonuclease is cleaved by the ribonuclease in the step (e) to form the cleaved fragment indicative of the presence of the target nucleic acid sequence.

According to a preferred embodiment, the ribonuclease used in the present invention is RNase H or Exo III.

Figure 4:
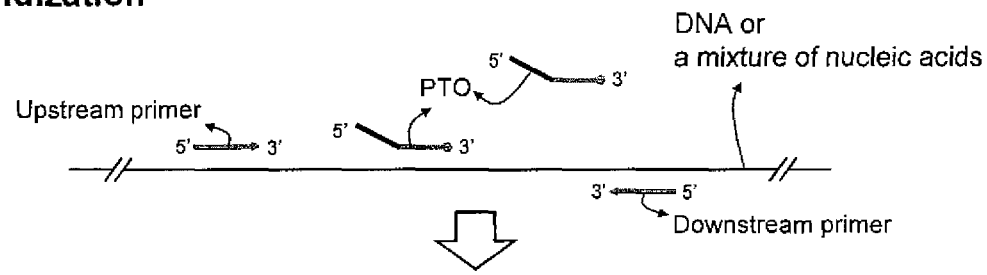
FIG. 4 represents schematically an embodiment of a PCEC assay using a cleavage site for RNase H.
Figure 4:
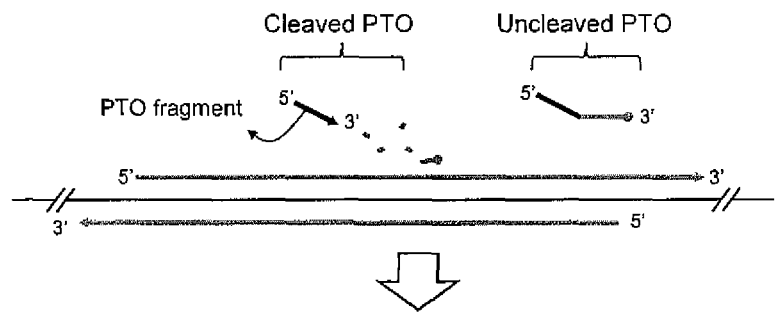
Figure 4:
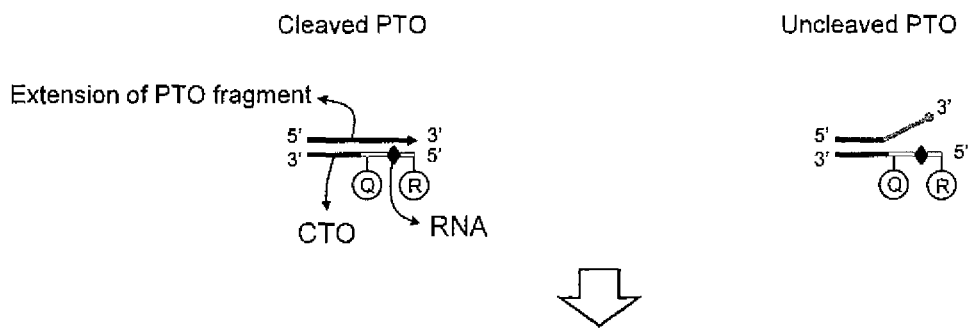
Figure 4:
Figure 7:
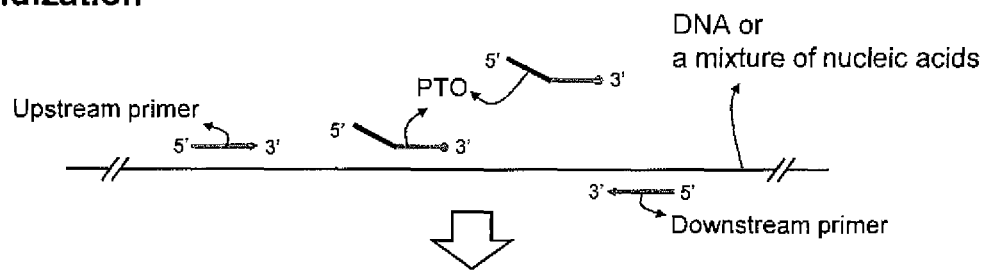
FIG. 7 represents schematically an embodiment of a PCEC assay using a cleavage site for RNase H.
Figure 7:
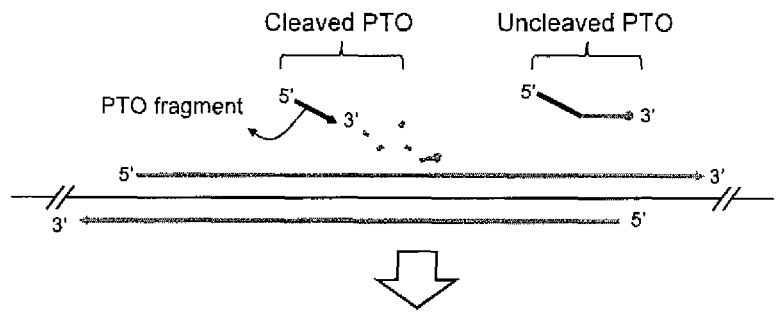
Figure 7:
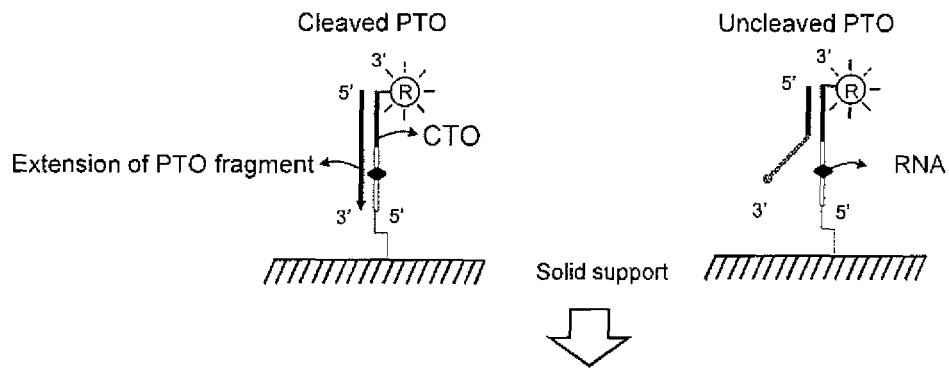
Figure 7:
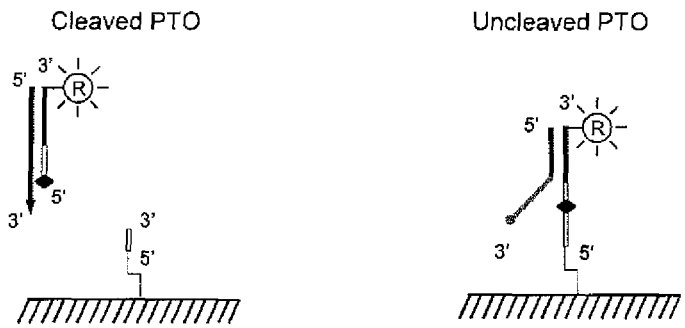
Figure 9:
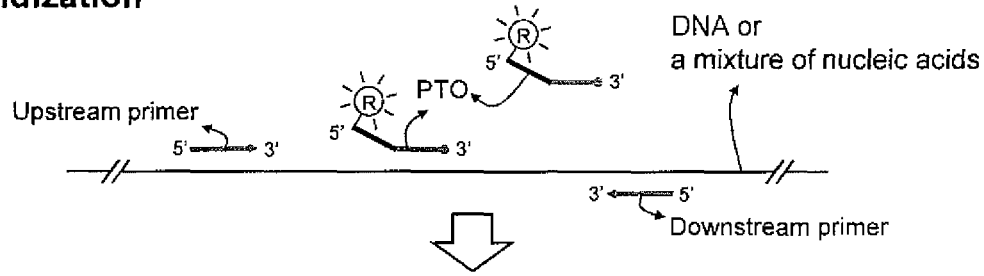
FIG. 9 represents schematically an embodiment of a PCEC assay using a cleavage site for RNase H.
Figure 9:
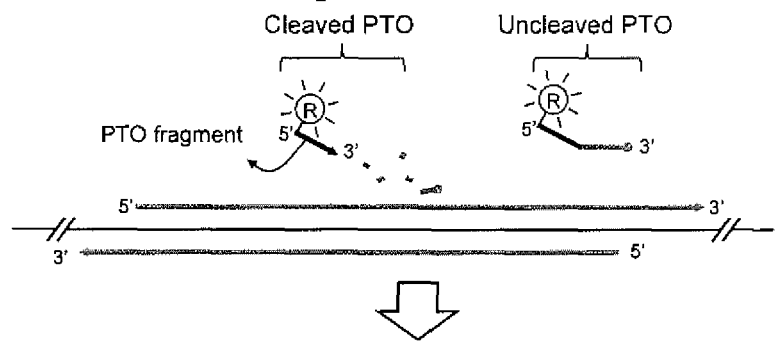
Figure 9:
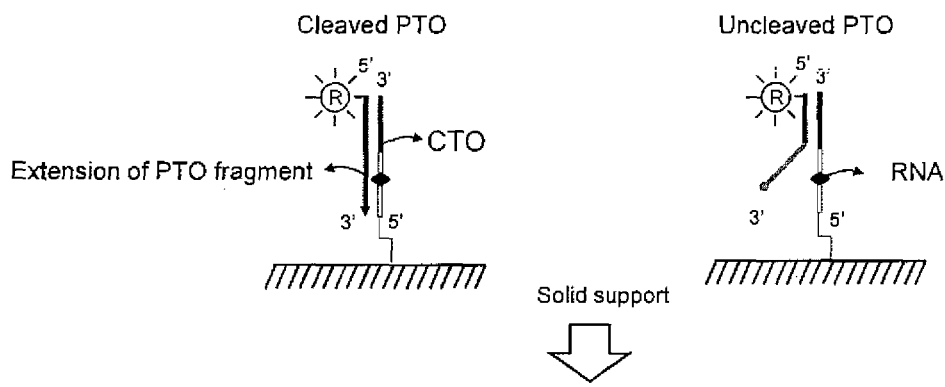
Figure 9:
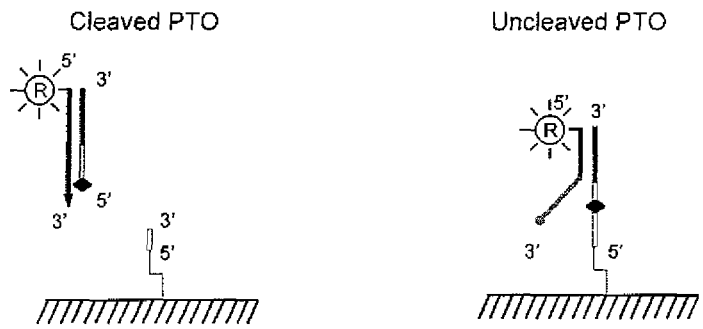

RNase H is one of endoribonucleases capable of digesting a RNA portion of a DNA-RNA hybrid duplex. Where RNase H is used, it is preferable that the CTO comprises a RNA molecule in its templating portion. As represented in FIGS. 4, 7 and 9, the PTO fragment formed by cleavage of the PTO hybridized with the target nucleic acid sequence is hybridized with the templating portion of the CTO and then extended to form a DNA-RNA hybrid extended duplex. RNase H endonucleolytically cleaves the DNA-RNA hybrid extended duplex to form the cleaved fragment indicating the presence of the target nucleic acid sequence.

Exo III has been reported to have RNase activities (Mol C D, et al., *Nature* 374(6520):381386 (1995)). Where Exo III is used, the cleaved fragment indicating the presence of the target nucleic acid sequence is formed in the same fashion as RNase H.

According to a preferred embodiment, the nucleolytic enzyme is a thermostable nucleolytic enzyme.

Step (e): Detection of Occurrence of the Cleavage of the Extended Duplex Indicating the Presence of the Target Nucleic Acid Sequence After the cleavage reaction of the extended duplex, the occurrence of the cleavage of the extended duplex is detected for determination of the presence of the target nucleic acid sequence.

The detection of the occurrence of the extended duplex cleavage may be performed in accordance with various procedures.

The occurrence of the extended duplex cleavage may be detected by directly analyzing the cleaved fragment of the extended duplex, e.g., by capillary electrophoresis. In such case, the PTO and/or CTO is preferably designed such that the cleaved fragment has a single fluorescent label, enabling to detect the cleaved fragment in more convenient manner.

According to a preferred embodiment, the detection of the occurrence of the extended duplex cleavage is carried out using signaling systems. The signaling system adopted to the present invention is characterized by synchronization of the extended duplex cleavage with a signal generation. In other words, the cleavage of the extended duplex induces to provide a detectable signal.

According to a preferred embodiment, the signaling system used in the present invention causes a signal change upon the cleavage of the extended duplex. Since the cleavage of the extended duplex occurs only when the target nucleic acid sequence is present, a signal indicating the presence of the target nucleic acid sequence is provided simultaneously with the signal change. In this regard, the present invention is carried out in a real-time manner, if desired.

According to a preferred embodiment, the extended duplex has at least one label, the label is derived from a label linked to the PTO or CTO or an intercalating dye, and the detection of the occurrence of the cleavage of the extended duplex is performed by detecting a signal from the at least one label.

Examples of labels suitable in the present invention will be described in more detail as follows:

(i) Single Label

The present invention may provide signal for the occurrence of the extended duplex cleavage indicating the presence of the target nucleic acid sequence by use of a single label.

The single label includes, but not limited to, a fluorescent label, a luminescent label, a chemiluminescent label and an electrochemical label. Preferably, the single label is a fluorescent label.

There are single labels showing different signals depending on whether they are linked to or released from oligonucleotides. When such single labels are used, the present invention may give a signaling system synchronized with the cleavage of the extended duplex even in a liquid phase. For example, a fluorescent terbium chelate provides different signals depending on whether it is linked to or released from oligonucleotides (Nurmi et al, *Nucleic Acids Research*, 2000, Vol. 28 No. 8 e28). For another example, where the single label is a dye emitting a polarized fluorescence through excitation by plane polarized light, the cleaved fragment may be detected by a fluorescence polarization (FP) method. The extent of the polarization of the emitted fluorescence is affected by motion of molecules linked to the label. Generally, as the motion becomes faster, the extent of the polarization becomes lower (Latif et al, *Genome Research*, 11:436-440, 2001).

According to a preferred embodiment, the CTO has the single label, the cleavage of the extended duplex in the step (e) form a cleaved fragment with the single label, a signal from the single label prior to the cleavage of the extended duplex is different from a signal from the single label after the cleavage of the extended duplex, and the difference in signals allow to detect the occurrence of the cleavage of the extended duplex.

According to a preferred embodiment, the PTO has the single label, the cleavage of the extended duplex in the step (e) form a cleaved fragment with the single label, a signal from the single label prior to the cleavage of the extended duplex is different from a signal from the single label after the cleavage of the extended duplex, and the difference in signals allow to detect the occurrence of the cleavage of the extended duplex.

According to a preferred embodiment, the single label providing differential signals dependent on the cleavage of the extended duplex is a fluorescent terbium chelate or a single label emitting a polarized fluorescence.

According to a preferred embodiment, the single label is linked to the CTO, more preferably the templating portion of the CTO, still more preferably to the 5'-end of the templating portion of the CTO.

According to a preferred embodiment, the single label is linked to the PTO, more preferably the 5'-tagging portion of the PTO. Preferably, the single label is positioned on the PTO such that the PTO fragment has the single label.

Where the present invention uses the single label, it is preferable that the present invention is performed on a solid phase using immobilized CTOs. In the case that the present invention employing the single label is performed on a solid phase, the single label linked to either the PTO or the CTO may provide signal indicating the occurrence of the cleavage of the extended duplex.

According to a preferred embodiment, the CTO is immobilized through its 5'-end or its 3'-end onto a solid substrate.

According to a preferred embodiment, the CTO has a single label, the cleavage of the extended duplex in the step (e) forms a cleaved fragment with the single label, the cleaved fragment is released from the solid substrate, thereby inducing a signal change on the solid substrate to provide a signal indicating the occurrence of the cleavage of the extended duplex.

More preferably, the CTO is immobilized through its 3'-end onto the solid substrate, the PTO has a single label, the cleavage of the extended duplex in the step (e) forms a cleaved fragment with the single label, the cleaved fragment is released from the solid substrate, thereby inducing a signal change on the solid substrate to provide a signal indicating the occurrence of the cleavage of the extended duplex.

Where the CTO is immobilized through its 3'-end onto a solid substrate and the single label is used, it is preferable that the single label is linked to the templating portion of the CTO and the cleavage site for the nucleolytic enzyme is generated for 5' to 3' exonuclease, restriction enzyme or ribonuclease.

As illustrated in FIG. 5, the PTO fragment is hybridized with the CTO immobilized through its 3'-end onto a solid substrate and extended to form the extended duplex, thereby generating the cleavage site for 5' to 3' exonuclease. The 5' to 3' exonuclease cleaves the extended duplex by attacking the cleavage site and releases a fluorescent reporter molecule from the 5'-end of the CTO. Where the target nucleic acid sequence is present, spots containing immobilized CTOs are observed to show decrease or extinguishment of fluorescence. In the absence of the target nucleic acid sequence, the decrease or extinguishment of fluorescence in spots containing immobilized CTOs are not observed.

Alternatively, the CTO is immobilized through its 5'-end onto the solid substrate, the PTO has a single label, the cleavage of the extended duplex in the step (e) forms a cleaved fragment with the single label, the cleaved fragment is released from the solid substrate, thereby inducing a signal change on the solid substrate to provide a signal indicating the occurrence of the cleavage of the extended duplex.

As represented in FIG. 6, the PTO fragment is hybridized with the CTO (comprising in its templating portion a sequence recognized by the restriction enzyme) immobilized through its 5'-end onto a solid substrate and extended to form the extended duplex, thereby generating the cleavage site for the restriction enzyme. The restriction enzyme cleaves the extended duplex and releases a fluorescent reporter molecule from the 3'-end of the CTO. Where the target nucleic acid sequence is present, spots containing immobilized CTOs are observed to show decrease or extinguishment of fluorescence. In the absence of the target nucleic acid sequence, the decrease or extinguishment of fluorescence in spots containing immobilized CTOs are not observed.

FIG. 7 represents examples using RNase H. The PTO fragment is hybridized with the CTO (comprising in its templating portion a RNA molecule) immobilized through its 5'-end onto a solid substrate and extended to form the extended duplex, thereby generating the cleavage site for RNase H. The RNase H cleaves the extended duplex and releases a fluorescent reporter molecule from the 3'-end of the CTO. Where the target nucleic acid sequence is present, spots containing immobilized CTOs are observed to show decrease or extinguishment of fluorescence. In the absence of the target nucleic acid sequence, the decrease or extinguishment of fluorescence in spots containing immobilized CTOs are not observed.

According to a preferred embodiment, the CTO is immobilized through its 5'-end onto the solid substrate, the PTO has a single label, the cleavage of the extended duplex in the step (e) forms a cleaved fragment with the single label, the cleaved fragment is released from the solid substrate, thereby inducing a signal change on the solid substrate to provide a signal indicating the occurrence of the cleavage of the extended duplex.

According to a preferred embodiment, the single label is linked to the PTO, more preferably the 5'-tagging portion of the PTO. Preferably, the single label is positioned on the PTO such that the PTO fragment has the single label.

FIGS. 8 and 9 represent examples using the PTO having a single label. In FIG. 8, the PTO fragment is hybridized with the CTO (comprising in its templating portion a sequence recognized by the restriction enzyme) immobilized through its 5'-end onto a solid substrate and extended to form the extended duplex, thereby generating the cleavage site for the restriction enzyme. The restriction enzyme cleaves the extended duplex and releases a fluorescent reporter molecule from the 5'-end of the PTO. Where the target nucleic acid sequence is present, spots containing immobilized CTOs are observed to show decrease or extinguishment of fluorescence. In the absence of the target nucleic acid sequence, the decrease or extinguishment of fluorescence in spots containing immobilized CTOs are not observed. In FIG. 9, the PTO fragment is hybridized with the CTO (comprising in its templating portion a RNA molecule) immobilized through its 5'-end onto a solid substrate and extended to form the extended duplex, thereby generating the cleavage site for RNase H. The RNase H cleaves the extended duplex and releases a fluorescent reporter molecule from the 5'-end of the PTO. Where the target nucleic acid sequence is present, spots containing immobilized CTOs are observed to show decrease or extinguishment of fluorescence. In the absence of the target nucleic acid sequence, the decrease or extinguishment of fluorescence in spots containing immobilized CTOs are not observed.

Where the CTO is immobilized through its 5'-end onto a solid substrate and the single label is used, it is preferable that the single label is linked to either CTO or PTO and the cleavage site for the nucleolytic enzyme such as restriction enzyme or ribonuclease is generated.

The single label used on the solid phase reaction requires no specific characteristics. For the solid phase reaction, any single label is useful because signal differentiation dependent on the occurrence of the cleavage of the extended duplex may be induced by remaining or non-remaining of the single label on the solid substrate after the cleavage of the extended duplex.

As discussed above, the presence of the target nucleic acid sequence may be detected by analyzing the presence, absence or change (increase or decrease) of signal from the single label that is associated with the second cleavage reaction.

The preferable examples of fluorescent single labels are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), DiI (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DilC(5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer.

Preferably, the fluorescent single label includes JOE, FAM, TAMRA, ROX and fluorescein-based label.

The single label may be linked to the CTO or PTO by conventional methods. Preferably, it is linked to the CTO or PTO through a spacer containing at least three carbon atoms (e.g., 3-carbon spacer, 6-carbon spacer or 12-carbon spacer).

According to a preferred embodiment, the single label linked to the CTO is located at its 5'-end or at 1-5 nucleotides apart from its 5'-end. Alternatively, the single label linked to the CTO is located at its 3'-end or at 1-5 nucleotides apart from its 3'-end.

According to a preferred embodiment, the single label linked to the PTO is located at its 5'-end or at 1-5 nucleotides apart from its 5'-end.

(ii) Interactive Dual Label

The interactive label system is a signal generating system in which energy is passed non-radioactively between a donor molecule and an acceptor molecule. As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent. In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent.

The donor molecule and the acceptor molecule may be described as a reporter molecular and a quencher molecule in the present invention, respectively.

Preferably, the signal indicative of the occurrence of the cleavage of the extended duplex (i.e., the presence of the target nucleic acid sequence) is generated by interactive label systems, more preferably the FRET label system (i.e., interactive dual label system).

According to a preferred embodiment, the interactive label is linked to the CTO.

According to a preferred embodiment, the cleavage site for the nucleolytic enzyme is positioned between the reporter molecule and the quencher molecule linked to the CTO, the quencher molecule quenches a signal from the reporter molecule prior to the formation of the extended duplex, the cleavage of the extended duplex separates the reporter molecule and the quencher molecule from each other and the occurrence of the cleavage of the extended duplex is detected by measuring a signal from the label.

The interactive label system in the present invention is useful in a liquid phase and on a solid phase.

Where the interactive label system is employed, it is preferable that the cleavage site generated in the step (d) is a cleavage site for 5' to 3' exonuclease, restriction enzyme or ribonuclease.

FIG. 2 represents the introduction of the cleavage site for 5' to 3' exonuclease by the formation of the extended duplex. The PTO fragment is hybridized with the CTO and extended to form the extended duplex, thereby generating the cleavage site for 5' to 3' exonuclease. The cleavage site for 5' to 3' exonuclease is positioned between the reporter molecule and the quencher molecule linked to the CTO.

Prior to the formation of the extended duplex, the quencher molecule is positioned at a site suitable to quench signal from the reporter molecule. Preferably, the quenching occurs when the two labels are adjacent along the length of the CTO or in a three-dimensional manner by the formation of conformational structures such as random coil and hairpin structure.

The 5' to 3' exonuclease cleaves the 5'-end of the extended duplex and releases a fluorescent reporter molecule to cause a signal change from fluorescent reporter molecule. The occurrence of the cleavage of the extended duplex is detected by measuring the fluorescent signal change for determination of the presence of the target nucleic acid sequence.

Where the quencher molecule is fluorescent, it is preferable signal from the quencher molecule is employed to be measured.

FIG. 3 represents the introduction of the cleavage site for restriction enzyme by the formation of the extended duplex. The PTO fragment is hybridized with the CTO and extended to form the extended duplex, thereby generating the cleavage site for restriction enzyme. The cleavage site for restriction enzyme is positioned between the reporter molecule and the quencher molecule linked to the CTO. The restriction enzyme cleaves the extended duplex by attacking the cleavage site and releases a fluorescent reporter molecule to cause a signal change from fluorescent reporter molecule. The occurrence of the cleavage of the extended duplex is detected by measuring the fluorescent signal change for determination of the presence of the target nucleic acid sequence.

FIG. 4 represents the introduction of the cleavage site for RNase by the formation of the extended duplex. The PTO fragment is hybridized with the CTO (comprising in its templating portion a RNA molecule) and extended to form the extended duplex, thereby generating the cleavage site for RNase. The cleavage site for RNase is positioned between the reporter molecule and the quencher molecule linked to the CTO. The RNase cleaves the extended duplex by attacking the cleavage site and releases a fluorescent reporter molecule to cause a signal change from fluorescent reporter molecule. The occurrence of the cleavage of the extended duplex is detected by measuring the fluorescent signal change for determination of the presence of the target nucleic acid sequence.

According to a preferred embodiment, at least one of the reporter molecule and the quencher molecule is linked to the templating portion of the CTO, more preferably the 5'-end of the CTO.

According to a preferred embodiment, both the reporter molecule and the quencher molecule are linked to the templating portion of the CTO.

According to a preferred embodiment, one of the reporter molecule and the quencher molecule is linked to the 5'-end of the CTO and the other to the 3'-end.

According to a preferred embodiment, either the reporter molecule or the quencher molecule linked to the templating portion of the CTO is located at its 5'-end or at 1-5 nucleotides apart from its 5'-end. For instance, the quencher molecule may be located at the 5'-end of the templating portion of the CTO or at 1-5 nucleotides apart from its 5'-end and the reporter molecule may be located at 5-50 nucleotides apart from the quencher molecule.

According to a preferred embodiment, the interactive dual label is located at a suitable position such that the quenching between the interactive dual label is maintained at the formation of the extended duplex and the unquenching between the interactive dual label is accomplished at release of the label by cleavage of the extended duplex.

In considering a real-time signal generation during the cleavage of the extended duplex, it is preferred that the reporter molecule and the quencher molecule are positioned at no more than 25 nucleotides, more preferably no more than 20 nucleotides, still more preferably no more than 15 nucleotides, still much more preferably no more than 10 nucleotides apart from each other. According to a preferred embodiment, the reporter molecule and the quencher molecule are separated by at least 3 nucleotides, more preferably at least 4 nucleotides, still more preferably at least 5 nucleotides, still much more preferably at least 6 nucleotides.

When the extended duplex is formed, the reporter molecule and the quencher molecule on the CTO may be conformationally separated to allow the quencher molecule to unquench the signal from the reporter molecule. The cleavage of the extended duplex completely separates the reporter molecule from the quencher molecule, enabling a signal change by the unquenching to become much higher.

Furthermore, because the cleaved fragment having a label (e.g., reporter molecule) is produced, the occurrence of the cleavage of the extended duplex may be analyzed by directly detecting a signal from the label linked to the cleaved fragment under more flexible or convenient conditions (e.g., high-stringent conditions or conditions after washing on a solid substrate).

According to a preferred embodiment, one of the interactive dual label linked to the immobilized CTO is remained on the solid substrate after the cleavage of the extended duplex.

According to a preferred embodiment, where the CTO immobilized onto the solid substrate has the interactive dual label and 5' to 3' exonuclease is used as nucleolytic enzymes, one of the interactive dual label may be securely remained on the solid substrate after the cleavage of the extended duplex by conferring suitable conditions for dissociating a fragment of the CTO from the duplex or conferring resistance to 5' to 3' exonuclease activities into internal nucleotides of the CTO.

According to a preferred embodiment, the resistance to 5' to 3' exonuclease activities is conferred by nucleotides having a backbone resistant to the 5' to 3' exonuclease activity, including various phosphorothioate linkages, phosphonate linkages, phosphoroamidate linkages and 2'-carbohydrates modifications, more preferably, phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage, aryl phosphoroamidate linkage, phosphoroselenate linkage, 2'-O-aminopropyl modification, 2'-O-alkyl modification, 2'-O-allyl modification, 2'-O-butyl modification, α-anomeric oligodeoxynucleotide and 1-(4'-thio-β-D-ribofuranosyl) modification.

The reporter molecule and the quencher molecule useful in the present invention may include any molecules known in the art. Examples of those can be described in detail with referring to descriptions for the fluorescent single label.

Suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition (Molecular Probes, Eugene, Oreg., 1996) U.S. Pat. Nos. 3,996,345 and 4,351,760.

It is noteworthy that a non-fluorescent black quencher molecule capable of quenching a fluorescence of a wide range of wavelengths or a specific wavelength may be used in the present invention. Examples of those are BHQ and DABCYL.

In the FRET label for the present invention, the reporter encompasses a donor of FRET and the quencher encompasses the other partner (acceptor) of FRET. For example, a fluorescein dye is used as the reporter and a rhodamine dye as the quencher.

(iii) Intercalating Label

The present invention may employ an intercalating label for association of the second cleavage reaction and signal generation indicative of the presence of the target nucleic acid sequence.

The intercalating label is more useful on a solid phase reaction using immobilized CTOs because double-stranded nucleic acid molecules present in samples can generate signals.

According to a preferred embodiment, the CTO is immobilized through its 5'-end or its 3'-end onto the solid substrate, an intercalating dye is used as a label, the cleavage of the extended duplex in the step (e) forms a cleaved fragment containing the intercalating dye, the cleaved fragment is released from the solid substrate, thereby inducing a signal change on the solid substrate to provide a signal indicating the occurrence of the cleavage of the extended duplex. In that case, it is preferable that the second cleavage reaction in the step (e) is performed using restriction enzymes or RNase.

According to a preferred embodiment, a cleaved fragment not immobilized onto the solid substrate is released from the solid substrate.

Exemplified intercalating dyes useful in this invention include SYBR™ Green I, PO-PRO™-1, BO-PRO™-1, SYTO™43, SYTO™44, SYTO™45, SYTOX™Blue, POPO™-1, POPO™-3, BOBO™-1, BOBO™-3, LO-PRO™-1, JO-PRO™-1, YO—PRO™1, TO-PRO™1, SYTO™ 11, SYTO™ 13, SYTO™ 15, SYTO™ 16, SYTO™20, SYTO™23, TOTO™-3, YOYO™3, GelStar™ and thiazole orange. The intercalating dyes intercalate specifically into double-stranded nucleic acid molecules to generate signals.

The PTO and CTO may be comprised of naturally occurring dNMPs. Alternatively, the PTO and CTO may be comprised of modified nucleotide or non-natural nucleotide such as PNA (peptide nucleic acid, see PCT Publication No. WO 92/20702) and LNA (locked nucleic acid, see PCT Publication Nos. WO 98/22489, WO 98/39352 and WO 99/14226). The PTO and CTO may comprise universal bases such as deoxyinosine, inosine, 1-(2'-deoxy-beta-D-ribofuranosyl)-3-nitropyrrole and 5-nitroindole. The term "universal base" refers to one capable of forming base pairs with each of the natural DNA/RNA bases with little discrimination between them.

As described above, the PTO may be cleaved at a site located in a 3'-direction apart from the 3'-end of the 5'-tagging portion of the PTO. The cleavage site may be located at the 5'-end part of the 3'-targeting portion of the PTO. Where the PTO fragment comprises the 5'-end part of the 3'-targeting portion of the PTO, a site of the CTO hybridized with the 5'-end part of the 3'-targeting portion may comprise a universal base, degenerate sequence or their combination. For instance, if the PTO is cleaved at a site located one nucleotide in a 3'-direction apart from the 3'-end of the 5'-tagging portion of the PTO, it is advantageous that the 5'-end part of the capturing portion of the CTO comprises a universal base for hybridization with the nucleotide. If the PTO is cleaved at a site located two nucleotides in a 3'-direction apart from the 3'-end of the 5'-tagging portion of the PTO, it is advantageous that the 5'-end of the capturing portion of the CTO comprises a degenerate sequence and its 3'-direction-adjacent nucleotide comprises a universal base. As such, where the cleavage of the PTO occurs at various sites of the 5'-end part of the 3'-targeting portion, the utilization of universal bases and degenerate sequences in the CTO is useful. In addition, where the PTOs having the same 5'-tagging portion are used for screening multiple target nucleic acid sequences under upstream primer extension-dependent cleavage induction, the PTO fragments having different 5'-end parts of the 3'-targeting portion may be generated. In such cases, universal bases and degenerate sequences are usefully employed in the CTO. The strategies using universal bases and degenerate sequences in the CTO ensure to use one type or minimal types of the CTO for screening multiple target nucleic acid sequences.

According to a preferred embodiment, the method further comprises repeating the steps (a)-(b), (a)-(d), (a)-(e) or (a)-(f) with denaturation between repeating cycles preferably, with a downstream primer. This repetition permits to amplify the target nucleic acid sequence and/or the target signal.

According to a preferred embodiment, the steps (a)-(b) and (c)-(f) or the steps (a)-(d) and (e)-(f) are performed in a reaction vessel or in separate reaction vessels.

According to a preferred embodiment, the method further comprises repeating the steps (a)-(b) or the steps (a)-(d) with denaturation between repeating cycles.

According to a preferred embodiment, the steps (a)-(f) are performed in a reaction vessel or in separate reaction vessels. For example, the steps (a)-(b), (c)-(d) or (e)-(f) may be performed in separate reaction vessels.

According to a preferred embodiment, the steps (a)-(b) and (c)-(f) may be simultaneously or separately even in a reaction vessel depending on reaction conditions (particularly, temperature).

It would be appreciated by one of skill in the art that repetition of certain steps, intervention of denaturation in repetition, separate performance of certain step(s) and time point of detection may be widely varied.

Where the repetition is performed using the upstream primer, it is preferable that the repetition is carried out in the presence of a downstream primer, preferably according to PCR. Where the repetition is performed using the upstream probe, it is preferable that the repetition is carried out in the presence of a downstream primer.

The present invention does not require that target nucleic acid sequences to be detected and/or amplified have any particular sequence or length, including any DNA (gDNA and cDNA) and RNA molecules.

Where a mRNA is employed as starting material, a reverse transcription step is necessary prior to performing an annealing step, details of which are found in Joseph Sambrook, et al., Molecular Cloning, A Laboratory Manual, Cold Spring Harbor Laboratory Press, Cold Spring Harbor, N.Y. (2001); and Noonan, K. F. et al., Nucleic Acids Res. 16:10366 (1988). For reverse transcription, a random hexamer or an oligo dT primer hybridizable to mRNA can be used.

The target nucleic acid sequences which may be detected and/or amplified include any naturally occurring prokaryotic, eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid.

The present invention is also useful in detection of a nucleotide variation. Preferably, the target nucleic acid sequence comprises a nucleotide variation. The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. The term nucleotide variation used herein includes any variation at a particular location in a DNA molecule. In other words, the term nucleotide variation includes a wild type and its any mutant type at a particular location in a DNA molecule.

In the present invention for detection of a nucleotide variation in a target nucleic acid sequence, where primers or probes used have a complementary sequence to the nucleotide variation in the target nucleic acid sequence, the target nucleic acid sequence containing the nucleotide variation is described herein as a matching template. Where primers or probes used have a non-complementary sequence to the nucleotide variation in the target nucleic acid sequence, the target nucleic acid sequence containing the nucleotide variation is described herein as a mismatching template.

For detection of nucleotide variations, the 3'-end of the upstream primer may be designed to be opposite to a site of a nucleotide variation in a target nucleic acid sequence. According to a preferred embodiment, the 3'-end of the upstream primer has a complementary sequence to the nucleotide variation in a target nucleic acid sequence. The 3'-end of the upstream primer having a complementary sequence to the nucleotide variation in the target nucleic acid sequence is annealed to the matching template and extended to induce cleavage of the PTO. The resultant PTO fragment is hybridized with the CTO to provide the target signal. In contrast, where the 3'-end of the upstream primer is mismatched to a nucleotide variation in a mismatching template, it is not extended under conditions that annealing of the 3'-end of primers is essential for extension even when the upstream primer is hybridized with the mismatching template, thereby resulting in no generation of the target signal.

Alternatively, it is possible to use PTO cleavage depending on the hybridization of PTO having a complementary sequence to a nucleotide variation in a target nucleic acid sequence. For example, under controlled conditions, a PTO having a complementary sequence to the nucleotide variation in the target nucleic acid sequence is hybridized with the matching template and then cleaved. The resultant PTO fragment is hybridized with the CTO to provide the target signal. While, under the controlled conditions, the PTO is not hybridized with a mismatching template having non-complementary sequence in the nucleotide variation position and not cleaved. Preferably, in this case, the complementary sequence to the nucleotide variation in the PTO is positioned at its middle of the 3'-targeting portion of the PTO.

Alternatively, the present invention uses the PTO having the nucleotide variation discrimination site positioned on the 5'-end part of the 3'-targeting portion for selectivity of the PTO to a specific nucleotide variation. The 5'-end part of the 3'-targeting portion of the PTO is positioned to a nucleotide variation in a target nucleic acid sequence for the detection of the nucleotide variation and the 5'-end part of the 3'-targeting portion of the PTO has a complementary sequence to the nucleotide variation in a target nucleic acid sequence.

Where the PTO is hybridized with the target nucleic acid sequence (i.e., match template) having the nucleotide variation complementary to the nucleotide variation discrimination site, the 5'-end part of the 3'-targeting portion forms a double strand with the match template; however, where the PTO is hybridized with a target nucleic acid sequence (i.e., mismatch template) having a nucleotide variation non-complementary to the nucleotide variation discrimination site, the 5'-end part of the 3'-targeting portion does not form a double strand with the mismatch template.

The term used herein "nucleotide variation discrimination site" with reference to the PTO is a complementary sequence on the 5'-end part of the 3'-targeting portion of the PTO to a nucleotide variation in a target nucleic acid sequence.

It is noteworthy that such distinct hybridization patterns on the nucleotide variation of interest are responsible for differences in initial cleavage sites of the PTO, thereby producing two types of PTO fragments to give signal differentiation depending on the presence of the nucleotide variation of interest.

In the presence and absence of the nucleotide variation of interest, a first fragment generated by cleavage of hybrid between the PTO and matching template and a second fragment generate by cleavage of hybrid between the PTO and mismatching template are produced, respectively. The second fragment comprises an additional 3'-end portion rendering the second fragment to be different from the first fragment.

In an embodiment for the detection of a single nucleotide variation, the 5'-end of the 3'-targeting portion of the PTO has a complementary sequence to the single nucleotide variation in a target nucleic acid sequence. As described above, the cleavage of the PTO hybridized with a matching template may be induced at a site immediately adjacent in a 3'-direction to the 5'-end of the 3'-targeting portion of the PTO, for example, under upstream primer extension-dependent cleavage induction. The 3'-end of the PTO fragment has the complementary nucleotide to the single nucleotide variation. The PTO fragment is hybridized with a CTO having a capturing portion comprising a sequence corresponding to the nucleotide variation and then extended to form the extended duplex, providing the target signal. If the same PTO is hybridized with a mismatching template having the identical sequence to the matching template except for the single nucleotide variation, the cleavage of the PTO may occur at a site two nucleotides apart in a 3'-direction from the 5'-end of the 3'-targeting portion of the PTO. The 3'-end of the PTO fragment has the further cleaved nucleotide than the complementary nucleotide to the single nucleotide variation. Where the site of the CTO hybridized with the additional-cleaved nucleotide is designed to have a non-complementary sequence to the further cleaved nucleotide, the 3'-end of the PTO fragment is not hybridized with the CTO, resulting in no extension of the PTO fragment in a controlled condition.

According to a preferred embodiment, a cleavage site of the PTO having a complementary sequence to the nucleotide variation at its 5'-end part of the 3'-targeting portion is different depending on hybridization with a matching template or with a mismatching template, such that the PTO fragment released from either hybridization event has different sequence preferably, in its 3'-end part, more preferably, in its 3'-end.

According to a preferred embodiment, the selection of the nucleotide sequence of CTO in consideration of the difference in 3'-end parts of the PTO fragments allows to discriminate the matching template from the mismatching template.

According to a preferred embodiment, the production of either the PTO fragments may be distinctly detected by an extension reaction on the CTO.

According to a preferred embodiment, the CTO has a sequence selected such that the CTO is not hybridized with the additional 3'-end portion of the second fragment to prevent the second fragment from extension when the second fragment is hybridized with the capturing portion of the CTO.

The extension of the first fragment is detected by occurrence of the cleavage of the extended duplex as described in the present invention.

According to a preferred embodiment, it is preferable that the 5'-end part of the 3'-targeting portion of the PTO comprises a non-base pairing moiety located within 1-10 nucleotides (more preferably 1-5 nucleotides) apart from the nucleotide variation discrimination site.

The non-base pairing moiety prevents the 5'-end part of the 3'-targeting portion from formation of a double strand with the target nucleotide sequence when the PTO is hybridized with the target nucleic acid sequence having the nucleotide variation non-complementary to the variation discrimination site.

The use of the non-base pairing moiety (e.g., mismatch nucleotide) enhances discrimination potential of the PTO to nucleotide variations.

According to a preferred embodiment, the non-base pairing moiety does not inhibit the formation of a double strand between the 5'-end part and the target nucleic acid sequence when the PTO is hybridized with the target nucleic acid sequence having the nucleotide variation complementary to the nucleotide variation discrimination site.

According to a preferred embodiment, the non-base pairing moiety widens the distance between the initial cleavage site on the hybrid of the PTO and the matching template and the initial cleavage site on the hybrid of the PTO and the mismatching template.

The non-base pairing moiety includes any moieties not forming a base pair between target nucleic acid sequences. Preferably, the non-base pairing moiety is (i) a nucleotide comprising an artificial mismatch base, a non-base pairing base modified to be incapable of base pairing or a universal base, (ii) a non-base pairing nucleotide modified to be incapable of base pairing, or (iii) a non-base pairing chemical compound.

For example, the non-base pairing moiety includes alkylene group, ribofuranosyl naphthalene, deoxy ribofuranosyl naphthalene, metaphosphate, phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage and aryl phosphoroamidate linkage. Conventional carbon spacers are also used as non-base pairing moieties. Universal bases as non-base pairing moieties are useful in adjusting cleavage sites of the PTO.

The non-base pairing moiety introduced into the 5'-end part has preferably 1-10, more preferably 1-5, still more preferably 1-2 moieties. A plurality of non-base pairing moieties in the 5'-end part may be present in a consecutive or intermittent manner. Preferably, the non-base pairing moiety has 2-5 consecutive moieties.

Preferably, the non-base pairing moiety is a non-base pairing chemical compound.

According to a preferred embodiment, the nucleotide variation discrimination site and the non-base pairing moiety of the PTO are located within 10 nucleotides (more preferably 8 nucleotides, 7 nucleotides, 6 nucleotides, 5 nucleotides, 4 nucleotides, 3 nucleotides, 2 nucleotides or 1 nucleotide, still more preferably 1 nucleotide) apart from the 5'-end of the 3'-targeting portion.

According to an embodiment, the PTO has a blocker portion containing as a blocker at least one nucleotide resistant to cleavage by the enzyme having 5' nuclease activity and the blocker portion is positioned at a site to be initially cleaved upon hybridization of the PTO with the mismatch template. The blocker portion prevents cleavage at the cleavage site and successive cleavages.

The number of blockers contained in the blocker portion may be not limited, preferably, 1-10, more preferably 2-10, still more preferably 3-8, most preferably 3-6 blockers. The blockers present in the probes may be in a continuous or intermittent manner, preferably a continuous manner. The nucleotides as blockers with a backbone resistant to the 5' to 3' exonuclease activity include any one known to one of skill in the art. For example, it includes various phosphorothioate linkages, phosphonate linkages, phosphoroamidate linkages and 2'-carbohydrates modifications. According to a more preferred embodiment, nucleotides having a backbone resistant to the 5' to 3' exonuclease include phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage, aryl phosphoroamidate linkage, phosphoroselenate linkage, 2'-O-aminopropyl modification, 2'-O-alkyl modification, 2'-O-allyl modification, 2'-O-butyl modification, α-anomeric oligodeoxynucleotide and 1-(4'-thio-β-D-ribofuranosyl) modification.

Where a conventional linear probe having at its 5'-end portion a nucleotide variation discrimination portion rather than a PTO is hybridized with a mismatch temple, its 5'-end portion may form a single strand under a certain condition. The probe may correspond to a PTO. The signal may be generated by PTO assay of the present invention. This approach may be useful in detection of a target nucleic acid sequence having a nucleotide variation non-complementary to the nucleotide variation discrimination site of probes.

According to a preferred embodiment, the target nucleic acid sequence used in the present invention is a pre-amplified nucleic acid sequence. The utilization of the pre-amplified nucleic acid sequence permits to significantly increase the sensitivity and specificity of target detection of the present invention.

According to a preferred embodiment, the method is performed in the presence of a downstream primer.

The advantages of the present invention may be highlighted in the simultaneous (multiplex) detection of at least two target nucleic acid sequences.

According to a preferred embodiment, the method is performed to detect at least two types (more preferably, at least three types, still more preferably at least five types) of target nucleic acid sequences.

According to a preferred embodiment, the method is performed to detect at least two types (more preferably, at least three types, still more preferably at least five types) of target nucleic acid sequences; wherein the upstream oligonucleotide comprises at least two types (more preferably at least three types, still more preferably at least five types) of oligonucleotides, the PTO comprises at least two types (more preferably at least three types, still more preferably at least five types) of the PTOs and the CTO comprises at least one type (preferably at least two types, more preferably at least three types, still more preferably at least five types) of the CTO.

The 5'-tagging portions of the at least two PTOs may have an identical sequence to each other. For instance, where the present invention is carried out for screening target nucleic acid sequences, the 5'-tagging portions of PTOs may have the identical sequence.

Furthermore, a single type of the CTO may used for detection of a plurality of target nucleic acid sequences. For example, where the PTOs having an identical sequence in their 5'-tagging portions are employed for screening target nucleic acid sequences, a single type of the CTO may used.

According to a preferred embodiment, the present invention is performed using at least two types of downstream primers.

The present invention may be carried out either in a liquid phase or on a solid phase.

Target Detection Using Immobilized CTO on a Solid Phase

According to a preferred embodiment, the present invention is performed on the solid phase and the CTO is immobilized through its 5'-end or 3'-end onto a solid substrate. In solid phase, the target signal provided on the solid substrate is measured.

When the CTO immobilized onto a solid substrate is used, chemical labels (e.g. biotin) or enzymatic labels (e.g. alkaline phosphatase, peroxidase, β-galactosidase and β-gluocosidase) may be used.

For the solid phase reaction, the CTO is immobilized directly or indirectly (preferably indirectly) through its 5'-end or 3'-end (preferably the 3'-end) onto the surface of the solid substrate. Furthermore, the CTO may be immobilized on the surface of the solid substrate in a covalent or non-covalent manner. Where the immobilized CTOs are immobilized indirectly onto the surface of the solid substrate, suitable linkers are used. The linkers useful in this invention may include any linkers utilized for probe immobilization on the surface of the solid substrate. For example, alkyl or aryl compounds with amine functionality, or alkyl or aryl compounds with thiol functionality serve as linkers for CTO immobilization. In addition, poly (T) tail or poly (A) tail may serve as linkers.

According to a preferred embodiment, the solid substrate used in the present invention is a microarray. The microarray to provide a reaction environment in this invention may include any those known to one of skill in the art. All processes of the present invention, i.e., hybridization to target nucleic acid sequences, cleavage, extension, melting and fluorescence detection, are carried out on the microarray. The immobilized CTOs on the microarray serve as hybridizable array elements. The solid substrate to fabricate microarray includes, but not limited to, metals (e.g., gold, alloy of gold and copper, aluminum), metal oxide, glass, ceramic, quartz, silicon, semiconductor, Si/SiO$_2$ wafer, germanium, gallium arsenide, carbon, carbon nanotube, polymers (e.g., polystyrene, polyethylene, polypropylene and polyacrylamide), sepharose, agarose and colloids. A plurality of immobilized CTOs in this invention may be immobilized on an addressable region or two or more addressable regions on a solid substrate that may comprise 2-1,000,000 addressable regions. Immobilized CTOs may be fabricated to produce array or arrays for a given application by conventional fabrication technologies such as photolithography, ink-jetting, mechanical microspotting, and derivatives thereof.

The present invention performed on the solid phase can detect simultaneously a plurality of target nucleic acid sequences even using a single type of a label because the labels on the CTOs immobilized are physically separated. In this regard, the number of target nucleic acid sequences to be detected by the present invention on the solid phase is not limited.

Using confocal detection devices, the signal only on the solid substrate may be detected without influence of labels suspended in a liquid phase.

In the present invention, a PTO fragment is produced by cleavage of the PTO hybridized with the target nucleic acid and it is annealed to and extended on the CTO, resulting in the formation of an extended strand.

It is also possible to provide additional fragments extendible on the CTO for enhancing the number of the extended strands by an additional 5' nuclease cleavage reaction using an additional PTO which comprises (i) a 3'-targeting portion comprising a hybridizing nucleotide sequence complementary to the extended strand and (ii) a 5'-tagging portion comprising a nucleotide sequence non-complementary to the extended strand but complementary to the capturing portion of the CTO. It is preferable to use an additional upstream oligonucleotide comprising a hybridizing nucleotide sequence complementary to the extended strand and being located upstream of the additional PTO for 5' nuclease cleavage reaction.

The above preferable embodiment has the feature that the formation of the additional fragments is dependent on the formation of an extended strand.

Alternatively, the additional fragments can be provided by using an additional PTO which comprises (i) a 3'-targeting portion comprising a hybridizing nucleotide sequence complementary to the templating portion of CTO and (ii) a 5'-tagging portion comprising a nucleotide sequence non-complementary to the templating portion of CTO but complementary to the capturing portion of the CTO.

According to a preferred embodiment, additional extended duplexes are formed by additional production of the extended strands, contributing to amplification of the target signal on the solid substrate.

Preferable Embodiment with Amplification of a Target Nucleic Acid Sequence

Preferably, the present invention is carried out simultaneously with amplification of a target nucleic acid sequence using a primer pair composed of an upstream primer and a downstream primer capable of synthesizing the target nucleic acid sequence.

In another aspect of this invention, there is provided a method for detecting a target nucleic acid sequence from a DNA or a mixture of nucleic acids by a PCEC (PTO Cleavage and Extension-Dependent Cleavage) assay, comprising:

(a) hybridizing the target nucleic acid sequence with a primer pair comprising an upstream primer and a downstream primer and a PTO (Probing and Tagging Oligonucleotide); wherein each of the upstream primer and the downstream primer comprise a hybridizing nucleotide sequence complementary to the target nucleic acid sequences; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the PTO is located between the upstream primer and the downstream primer; wherein the PTO is blocked at its 3'-end to prohibit its extension;

(b) contacting the resultant of the step (a) to a template-dependent nucleic acid polymerase having a 5' nuclease activity under conditions for extension of the primers and for cleavage of the PTO; wherein when the PTO is hybridized with the target nucleic acid sequence, the upstream primer is extended and the extended strand induces cleavage of the PTO by the template-dependent nucleic acid polymerase having the 5' nuclease activity such that the cleavage releases a fragment comprising the 5'-tagging portion or a part of the 5'-tagging portion of the PTO;

(c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO;

(d) performing an extension reaction using the resultant of the step (c) and the template-dependent nucleic acid polymerase; wherein the fragment hybridized with the capturing portion of the CTO is extended to form an extended duplex and to generate a cleavage site for a nucleolytic enzyme;

(e) cleaving the extended duplex using the nucleolytic enzyme to form a cleaved fragment; and (f) detecting the occurrence of the cleavage of the extended duplex; whereby the occurrence of the cleavage of the extended duplex indicates the presence of the target nucleic acid sequence.

Since the preferable embodiment of the present invention follows the steps of the present method described above, the common descriptions between them are omitted in order to avoid undue redundancy leading to the complexity of this specification.

According to a preferred embodiment, the method further comprise repeating the steps the steps (a)-(b), (a)-(d), (a)-(e) or (a)-(f) with denaturation between repeating cycles. The reaction repetition is accompanied with amplification of the target nucleic acid sequence. Preferably, the amplification is performed in accordance with PCR (polymerase chain reaction) which is disclosed in U.S. Pat. Nos. 4,683,195, 4,683,202, and 4,800,159.

According to a preferred embodiment, the method is performed to detect at least two types of target nucleic acid sequences.

Kits for Target Detection

In still another aspect of this invention, there is provided a kit for detecting a target nucleic acid sequence from a DNA or a mixture of nucleic acids by a PCEC (PTO Cleavage and Extension-Dependent Cleavage) assay, comprising:

(a) a PTO (Probing and Tagging Oligonucleotide); wherein the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence;

(b) an upstream oligonucleotide; wherein the upstream oligonucleotide comprises a hybridizing nucleotide sequence complementary to the target nucleic acid sequence; wherein the upstream oligonucleotide is located upstream of the PTO; wherein the upstream oligonucleotide or its extended strand induces cleavage of the PTO by an enzyme having a 5' nuclease activity to release a fragment comprising the 5'-tagging portion or a part of the 5'-tagging portion of the PTO; and (c) a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO; wherein the fragment hybridized with the capturing portion of the CTO is extended to form an extended duplex and to generate a cleavage site for a nucleolytic enzyme.

Since the kit of this invention is constructed to perform the detection method of the present invention described above, the common descriptions between them are omitted in order to avoid undue redundancy leading to the complexity of this specification.

According to a preferred embodiment, the kit further comprises an enzyme having a 5' nuclease activity for cleaving the PTO hybridized with the target nucleic acid sequence.

According to a preferred embodiment, the kit further comprises a nucleolytic enzyme for cleavage of an extended duplex formed by extension of the fragment hybridized with the capturing portion of the CTO.

According to a preferred embodiment, the nucleolytic enzyme is a 5' to 3' exonuclease, a restriction enzyme or a ribonuclease.

According to a preferred embodiment, the nucleolytic enzyme is a restriction enzyme, the templating portion of the CTO comprises a sequence recognized by the restriction enzyme and the formation of the extended duplex generates a cleavage site of the restriction enzyme.

According to a preferred embodiment, the nucleolytic enzyme is a ribonuclease, the templating portion of the CTO comprises a RNA sequence and the formation of the extended duplex produces the DNA-RNA hybrid duplex to generate a cleavage site of the ribonuclease.

According to a preferred embodiment, the nucleolytic enzyme is a 5' to 3' exonuclease and the formation of the extended duplex generates on the CTO a cleavage site of the 5' to 3' exonuclease.

According to a preferred embodiment, the cleavage site for the nucleolytic enzyme is a cleavage site for a nucleolytic enzyme capable of cleaving a DNA duplex, a RNA duplex or a DNA-RNA hybrid duplex.

According to a preferred embodiment, the ribonuclease is RNase H or Exo III.

According to a preferred embodiment, the 5' to 3' exonuclease is a template-dependent DNA polymerase having a 5' to 3' exonuclease activity.

According to a preferred embodiment, the nucleolytic enzyme is a thermostable nucleolytic enzyme.

According to a preferred embodiment, the extended duplex has at least one label, the label is derived from a label linked to the PTO or CTO or an intercalating dye, and the detection of the occurrence of the cleavage of the extended duplex is performed by detecting a signal from the at least one label.

According to a preferred embodiment, the CTO has the single label, the cleavage of the extended duplex form a cleaved fragment with the single label, a signal from the single label prior to the cleavage of the extended duplex is different from a signal from the single label after the cleavage of the extended duplex, and the difference in signals allow to detect the occurrence of the cleavage of the extended duplex.

According to a preferred embodiment, the single label is a fluorescent label.

According to a preferred embodiment, the cleavage site for the nucleolytic enzyme is positioned between the reporter molecule and the quencher molecule linked to the CTO, the quencher molecule quenches a signal from the reporter molecule prior to the formation of the extended duplex, the cleavage of the extended duplex separates the reporter molecule and the quencher molecule from each other and the occurrence of the cleavage of the extended duplex is detected by measuring a signal from the label.

According to a preferred embodiment, at least one of the reporter molecule and the quencher molecule is linked to the 5'-end of the CTO.

According to a preferred embodiment, the CTO is immobilized through its 5'-end or its 3'-end onto a solid substrate.

According to a preferred embodiment, the CTO has a single label, the cleavage of the extended duplex forms a cleaved fragment with the single label, the cleaved fragment is released from the solid substrate, thereby inducing a signal change on the solid substrate to provide a signal indicating the occurrence of the cleavage of the extended duplex.

According to a preferred embodiment, the CTO is immobilized through its 5'-end onto the solid substrate, the PTO has a single label, the cleavage of the extended duplex forms a cleaved fragment with the single label, the cleaved fragment is released from the solid substrate, thereby inducing a signal change on the solid substrate to provide a signal indicating the occurrence of the cleavage of the extended duplex.

According to a preferred embodiment, the single label is a fluorescent label.

According to a preferred embodiment, the CTO is immobilized through its 5'-end or its 3'-end onto the solid substrate, an intercalating dye is used as a label, the cleavage of the extended duplex forms a cleaved fragment containing the intercalating dye, the cleaved fragment is released from the solid substrate, thereby inducing a signal change on the solid substrate to provide a signal indicating the occurrence of the cleavage of the extended duplex.

According to a preferred embodiment, the PTO and/or CTO is blocked at its 3'-end to prohibit its extension.

According to a preferred embodiment, the upstream oligonucleotide is an upstream primer or an upstream probe.

According to a preferred embodiment, the upstream oligonucleotide is located adjacently to the PTO to the extent that the upstream oligonucleotide induces cleavage of the PTO by the enzyme having the 5' nuclease activity.

According to a preferred embodiment, the upstream primer induces through its extended strand the cleavage of the PTO by the enzyme having the 5' nuclease activity.

According to a preferred embodiment, the capturing portion of the CTO comprises at its 5'-end part a nucleotide sequence complementary to a part of the 3'-targeting portion of the PTO.

According to a preferred embodiment, the nucleotide sequence complementary to the part of the 3'-targeting portion of the PTO is 1-5 nucleotides in length.

According to a preferred embodiment, the kit is used to detect at least two types of target nucleic acid sequences; wherein the upstream oligonucleotide comprises at least two types of oligonucleotides, the PTO comprises at least two types of the PTOs and the CTO comprises at least two types of the CTOs.

According to a preferred embodiment, the 5'-tagging portions of the at least two types of PTOs have the identical sequence to each other or different sequences from each other.

According to a preferred embodiment, the upstream oligonucleotide is an upstream primer and the kit further comprises a template-dependent nucleic acid polymerase for the extension of the upstream primer.

According to a preferred embodiment, the enzyme having the 5' nuclease activity is a thermostable DNA polymerase having a 5' nuclease activity or FEN nuclease.

According to a preferred embodiment, the kit further comprises a downstream primer.

All of the present kits described hereinabove may optionally include the reagents required for performing target amplification PCR reactions (e.g., PCR reactions) such as buffers, DNA polymerase cofactors, and deoxyribonucleotide-5-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The kits, typically, are adopted to contain the constituents aforedescribed in separate packaging or compartments.

The features and advantages of this invention will be summarized as follows:

(a) The present invention is characterized by generating a cleavage site for a nucleolytic enzyme on the extended duplex of which the formation is dependent on the presence of a target nucleic acid sequence. The present invention detects the occurrence of the cleavage of the extended duplex, thereby determining the presence of the target nucleic acid sequence.

(b) Various methods may be employed for detection of the occurrence of the cleavage of the extended duplex by nucleolytic enzymes. In considering the cleavage site on the extended duplex, a single label, an interactive dual label or an intercalating label may be intriguingly adopted for generating signals indicating the presence of target nucleic acid sequences. In these connections, the present invention is very applicable to real-time detection of target nucleic acid sequences.

(c) Since the extended duplex is cleaved in the present method, there is no limitation generally encountered in conventional methods using conditions for maintaining duplex structures. Therefore, the detection of target nucleic acid sequences in the present method may be carried out under a wide variety of conditions (e.g., a relatively wide range of temperatures).

(d) It is noteworthy that the sequence of the 5'-tagging portion of PTO and the sequence of CTO can be selected with no consideration of target nucleic acid sequences. This makes it possible to pre-design a pool of sequences for the 5'-tagging portion of PTO and CTO. Although the 3'-targeting portion of the PTO has to be prepared with considering target nucleic acid sequences, the CTO can be prepared in a ready-made fashion with no consideration or knowledge of target nucleic acid sequences. Such features provide prominent advantages in multiple target detection, inter alia, on a microarray assay using CTOs immobilized onto a solid substrate.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Evaluation of PTO Cleavage and Extension-Dependent Cleavage (PCEC) Assay Using 5' to 3' Exonuclease A new assay, PTO Cleavage and Extension-dependent Cleavage (PCEC) assay, was evaluated for the detection of a target nucleic acid sequence using 5' to 3' exonuclease activity of Taq DNA polymerase (see FIG. 2).

Taq DNA polymerase having a 5' nuclease activity was used for the extension of upstream primer, the cleavage of PTO and the extension of PTO fragment. Furthermore, Taq DNA polymerase having a 5' nuclease activity was used for the cleavage of the extended duplex.

PTO and CTO are blocked with a carbon spacer at their 3'-ends. PTO has no label. CTO has a fluorescent reporter molecule (FAM) at its 5'-end and a quencher molecule (BHQ-1) in its templating portion. The extended duplex formed during the assay has the interactive dual label. The extended duplex has a cleavage site susceptible to 5' nuclease activity of the Taq DNA polymerase at it 5'-end portion. The 5'-end labeled with FAM is cleaved by the 5' nuclease activity of Taq DNA polymerase and the FAM is separated from the BHQ-1. The synthetic oligonucleotide for *Neisseria gonorrhoeae* (NG) gene was used as a target template.

The sequences of synthetic template, upstream primer, PTO and CTO used in this Example are:

```
                                            (SEQ ID NO: 1)
NGT     5'-AAATATGCGAAACACGCCAATGAGGGGCATGATG
        CTTTCTTTTTGTTCTTGCTCGGCAGAGCGAGTGATA
        CCGATCCATTGAAAAA-3'

(SEQ ID NO: 2)
NG-R    5'-CAATGGATCGGTATCACTCGC-3'

(SEQ ID NO: 3)
NG-PTO-1 5'-ACGACGGCTAGGCTTTACTGCCCCTCATTGGCG
         TGTTTCG[C3 spacer]-3'

(SEQ ID NO: 4)
NG-CTO-1 5'-[FAM]CCTCCTCCTCCTCC[T(BHQ-1)]
         CCAGTAAAGCCTAGCCGTCGT[C3 spacer]-3'

(Underlined letters indicate the
5'-tagging portion of PTO)
```

The reaction was conducted in the final volume of 20 µl containing 2 pmole of synthetic template (SEQ ID NO: 1) for NG gene, 10 pmole of upstream primer (SEQ ID NO: 2), 5 pmole of PTO (SEQ ID NO: 3), 2.5 pmole of CTO (SEQ ID NO: 4) and 10 µl of 2× Master Mix containing 2.5 mM $MgCl_2$, 200 µM of dNTPs and 1.6 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 60 cycles of 30 sec at 95° C., 63 sec at 60° C., and 30 sec at 72° C. Detection of the generated signal was performed at the denaturation step (95° C.) of each cycle. The detection at the denaturation step allows verifying whether a signal is generated by separation of the dual label subject to cleavage of the extended duplex.

Figure 10:
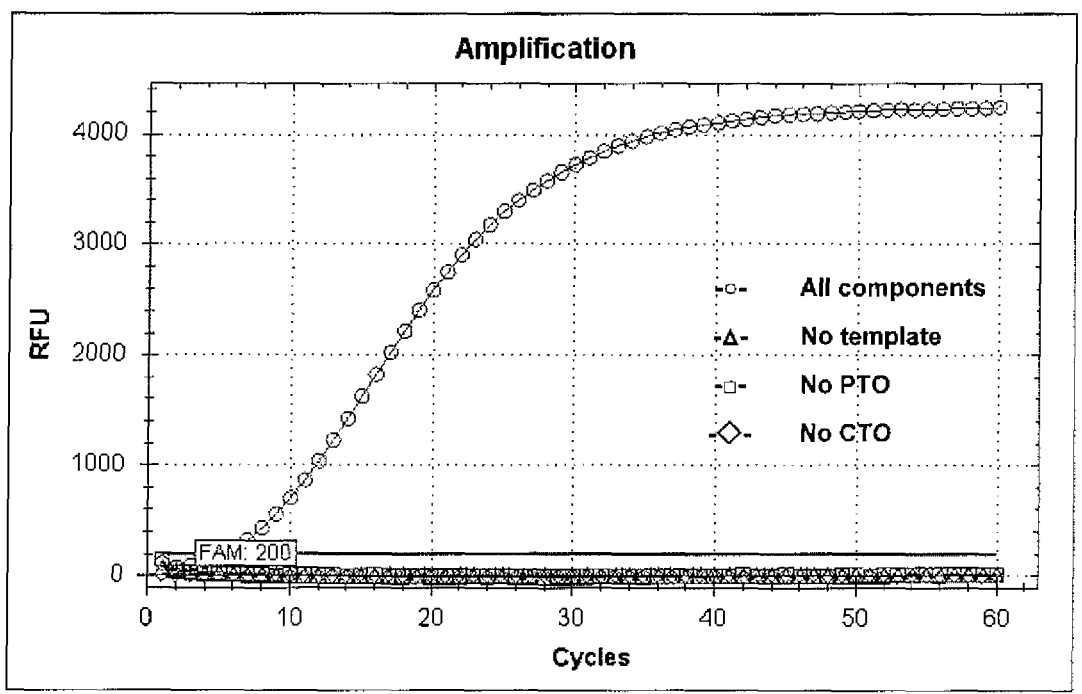
FIG. 10 shows the results of the real-time detection of *Neisseria gonorrhoeae* gene by a PCEC assay. The CTO has a reporter molecule and a quencher molecule at its templating portion.

As shown FIG. 10, the fluorescent signal was detected in the presence of the template. No signal was detected in the absence of the template, PTO or CTO.

These results indicate that a target nucleic acid sequence can be detected by PCEC assay using 5' to 3' exonuclease.

Example 2: Evaluation of PCEC Assay Using Restriction Enzyme

We further evaluated PCEC assay for the detection of a target nucleic acid sequence using restriction enzyme (see FIG. 3).

Taq DNA polymerase having a 5' nuclease activity was used for the extension of upstream primer, the cleavage of PTO and the extension of PTO fragment. Thermostable restriction enzyme (PspGI) was used for the cleavage of the extended duplex.

PTO and CTO are blocked with a carbon spacer at their 3'-ends. PTO has no label. CTO has a fluorescent reporter molecule (Cal Fluoro Red 610) at its 5'-end and has a quencher molecule (BHQ-1) in its templating portion. The CTO is designed to provide a restriction enzyme cleavage site for PspGI on the formation of an extended duplex. The extended duplex formed during the assay has the interactive dual label separated by the restriction enzyme cleavage site. The cleavage at the restriction enzyme site results in separation of the fluorescent reporter molecule (Cal Fluoro Red 610) from the quencher molecule (BHQ-1).

For one's own information, the 5'-end labeled with Cal Fluoro Red 610 in an extended duplex is resistant to the upstream oligonucleotide independent 5' nuclease activity of Taq DNA polymerase.

The synthetic oligonucleotide for *Neisseria gonorrhoeae* (NG) gene was used as a target template.

The sequences of synthetic template, upstream primer, PTO and CTO used in this Example are:

```
                                            (SEQ ID NO: 1)
NGT     5'-AAATATGCGAAACACGCCAATGAGGGGCATG
        ATGCTTTCTTTTTGTTCTTGCTCGGCAGAGCGAG
        TGATACCGATCCATTGAAAAA-3'

(SEQ ID NO: 2)
NG-R    5'-CAATGGATCGGTATCACTCGC-3'

(SEQ ID NO: 5)
NG-PTO-2 5'-ACGACGGCTTGGCCCCTCATTGGCGTGTTTCG
        [C3 spacer]-3'
```

```
                                            (SEQ ID NO: 6)
NG-CTO-2 5'-[CAL Fluor Red 610]CCTCCTGGCCCTCCTCC
        [T(BHQ-2)]CCTCCAGTAAAGCCAAGCCGTCGT
        [C3 Spacer]-3'
```

(Underlined letters indicate the 5'-tagging portion of PTO)
(Bold letters indicate restriction enzyme cleavage site for PspGI)

The reaction was conducted in the final volume of 20 μl containing 2 pmole of synthetic template (SEQ ID NO: 1) for NG gene, 10 pmole of upstream primer (SEQ ID NO: 2), 5 pmole of PTO (SEQ ID NO: 5), 2 pmole of CTO (SEQ ID NO: 6) and 10 μl of 2× Master Mix containing 2.5 mM $MgCl_2$, 200 μM of dNTPs and 1.6 units of H-Taq DNA polymerase (Solgent, Korea) and 1 unit of PspGI (New England Biolabs, US); the tube containing the reaction mixture was placed in the real-time thermocycler (CFX96, Bio-Rad); the reaction mixture was denatured for 15 min at 95° C. and subjected to 60 cycles of 30 sec at 95° C., 63 sec at 60° C., 30 sec at 72° C. Detection of the generated signal was performed at the denaturation step (95° C.) of each cycle.

The fluorescent signal was detected in the presence of the template. No signal was detected in the absence of the template, PTO or CTO.

These results indicate that a target nucleic acid sequence can be detected by PCEC assay using restriction enzyme.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for detecting a target nucleic acid sequence from a DNA sample or a mixture of nucleic acids by a Probing and Tagging Oligonucleotide (PTO) Cleavage and Extension-Dependent Cleavage (PCEC) assay, comprising:

(a) hybridizing the target nucleic acid sequence in a DNA sample or a mixture of nucleic acids with an upstream oligonucleotide and a PTO, thereby forming a target nucleic acid sequence hybridized with the upstream oligonucleotide and the PTO if the target nucleic acid sequence is present in the DNA sample or the mixture of nucleic acids; wherein the upstream oligonucleotide comprises a hybridizing nucleotide sequence complementary to the target nucleic acid sequence; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; wherein when the upstream oligonucleotide and the PTO are both hybridized with the target nucleic acid sequence, the upstream oligonucleotide is hybridized upstream of the PTO; wherein the PTO is blocked at its 3'-end to prohibit its extension;

(b) contacting the target nucleic acid sequence hybridized with the upstream oligonucleotide and the PTO of the step (a) to a DNA polymerase having a 5' nuclease activity under conditions for extension of the upstream oligonucleotide and cleavage of the PTO such that said cleavage of the PTO by the DNA polymerase having the 5' nuclease activity generates a fragment comprising the 5'-tagging portion or a part of the 5'-tagging portion of the PTO if the target nucleic acid sequence is present in the DNA sample or the mixture of nucleic acids;

(c) hybridizing the fragment comprising the 5'-tagging portion or a part of the 5'-tagging portion of the PTO with a Capturing and Templating Oligonucleotide (CTO) if the target nucleic acid sequence is present in the DNA sample or the mixture of nucleic acids; wherein the CTO comprises in a 3' to 5' direction (i) a capturing portion comprising a nucleotide sequence complementary to the 5'-tagging portion or the part of the 5'-tagging portion of the PTO and non-complementary to the 3'-targeting portion of the PTO and (ii) a templating portion comprising a nucleotide sequence non-complementary to the 5'-tagging portion and the 3'-targeting portion of the PTO; wherein the CTO has no hairpin structure; wherein the CTO has a single fluorescent label or an interactive dual label comprising a fluorescent reporter molecule and a quencher molecule at its templating portion; wherein the fragment comprising the 5'-tagging portion or a part of the 5'-tagging portion of the PTO is hybridized with the capturing portion of the CTO such that a hybridized complex formed by the fragment comprising the 5'-tagging portion or a part of the 5'-tagging portion of the PTO and the CTO is produced; wherein the CTO is blocked at its 3'-end to prohibit its extension;

(d) performing an extension reaction in the presence of the hybridized complex of the step (c) and the DNA polymerase having the 5' nuclease activity if the target nucleic acid sequence is present in the DNA sample or the mixture of nucleic acids; wherein the hybridized complex of the step (c) is extended such that an extended duplex having the single fluorescent label or the interactive dual label comprising a fluorescent reporter molecule and a quencher molecule is formed; wherein the extended duplex can be cleaved by (i) a restriction enzyme, wherein a cleavage site recognized by the restriction enzyme is present in the templating portion of the CTO; or (ii) a 5' to 3' exonuclease capable of cleaving the CTO of the extended duplex but not cleaving the CTO in a single-stranded state;

(e) forming a cleaved fragment by cleaving the extended duplex using the restriction enzyme or the 5' to 3' exonuclease if the target nucleic acid sequence is present in the DNA sample or the mixture of nucleic acids;

when the extended duplex has the single fluorescent label, the method is performed on a solid substrate on which the CTO is immobilized, the single fluorescent label is linked to the templating portion of the CTO, the cleaved fragment is with the single fluorescent label, and the cleaved fragment is released from the solid substrate; wherein when the CTO is immobilized through its 5'-end onto the solid substrate, the cleavage site for the restriction enzyme is located between the 5'-end of the CTO and the position of the single fluorescent label of the CTO, and when the CTO is immobilized through its 3'-end onto the solid substrate, the cleavage site for the restriction enzyme is located between the 3'-end of the CTO and the position of the single fluorescent label of the CTO;

when the extended duplex has said interactive dual label comprising a fluorescent reporter molecule and a quencher molecule, the quencher molecule of the CTO quenches a fluorescent signal from the fluorescent reporter molecule of the CTO prior to the formation of the hybridized complex of the step (c) and after formations of the hybridized complex of the step (c) and the extended duplex, the fluorescent reporter molecule and the quencher molecule of the CTO are separated by cleavage at the cleavage site of the CTO by the restriction enzyme or by sequential cleavage from the 5'-end of the CTO by the 5' to 3' exonuclease, wherein the cleavage site for the restriction enzyme is located between the fluorescent reporter molecule of the CTO and the quencher molecule of the CTO; and (f) detecting the target nucleic acid sequence from the DNA sample or the mixture of nucleic acids, wherein detecting a fluorescent signal from the single fluorescent label of the cleaved fragment or the fluorescent reporter molecule separated from the quencher molecule of the extended duplex indicates the presence of the target nucleic acid sequence in the DNA sample or the mixture of nucleic acids.

2. The method according to claim 1, wherein the DNA polymerase having the 5' nuclease activity has a 5' to 3' exonuclease activity.

3. The method according to claim 1, wherein the upstream oligonucleotide is an upstream primer or an upstream probe.

4. The method according to claim 1, wherein the method further comprises repeating the steps (a)-(b), (a)-(d), (a)-(e) or (a) (f) after step (f).

5. The method according to claim 1, wherein the upstream oligonucleotide is an upstream primer.

6. The method according to any one of claims 1, 2, 3, 4, and 5, wherein step (a) is performed in the presence of a downstream primer.

7. A method for detecting a target nucleic acid sequence from a DNA sample or a mixture of nucleic acids by a Probing and Tagging Oligonucleotide (PTO) Cleavage and Extension-Dependent Cleavage (PCEC) assay, comprising:

(a) hybridizing the target nucleic acid sequence in a DNA sample or a mixture of nucleic acids with an upstream primer a downstream primer and a PTO, thereby forming a target nucleic acid sequence hybridized with the upstream primer, the downstream primer and the PTO if the target nucleic acid sequence is present in the DNA sample or the mixture of nucleic acids; wherein each of the upstream primer and the downstream primer comprises a hybridizing nucleotide sequence complementary to the target nucleic acid sequence; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; wherein when the upstream primer, the downstream primer and the PTO are hybridized with the target nucleic acid sequence, the PTO is hybridized with a region of the target nucleic acid sequence between a region of the target nucleic acid sequence which the upstream primer is hybridized and a region of the target nucleic acid sequence which the downstream primer is hybridized; wherein the PTO is blocked at its 3'-end to prohibit its extension;

(b) contacting the target nucleic acid sequence hybridized with the upstream primer, the downstream primer and the PTO of the step (a) to a DNA polymerase having a 5' nuclease activity under conditions for extension of the primers and cleavage of the PTO such that said cleavage of the PTO by the DNA polymerase having the 5' nuclease activity generates a fragment comprising the 5'-tagging portion or a part of the 5'-tagging portion of the PTO if the target nucleic acid sequence is present in the DNA sample or the mixture of nucleic acids;

(c) hybridizing the fragment comprising the 5'-tagging portion or a part of the 5'-tagging portion of the PTO with a Capturing and Templating Oligonucleotide (CTO) if the target nucleic acid sequence is present in the DNA sample or the mixture of nucleic acids; wherein the CTO comprises in a 3' to 5' direction (i) a capturing portion comprising a nucleotide sequence complementary to the 5'-tagging portion or the part of the 5'-tagging portion of the PTO and non-complementary to the 3'-targeting portion of the PTO and (ii) a templating portion comprising a nucleotide sequence non-complementary to the 5'-tagging portion and the 3'-targeting portion of the PTO; wherein the CTO has no hairpin structure; wherein the CTO has a single fluorescent label or an interactive dual label comprising a fluorescent reporter molecule and a quencher molecule at its templating portion; wherein the fragment comprising the 5'-tagging portion or a part of the 5'-tagging portion of the PTO is hybridized with the capturing portion of the CTO such that a hybridized complex formed by the fragment comprising the 5'-tagging portion or a part of the 5'-tagging portion of the PTO and the CTO is produced; wherein the CTO is blocked at its 3'-end to prohibit its extension;

(d) performing an extension reaction in the presence of the hybridized complex of the step (c) and the DNA polymerase having the 5' nuclease activity if the target nucleic acid sequence is present in the DNA sample or the mixture of nucleic acids; wherein the hybridized complex of the step (c) is extended such that an extended duplex having the single fluorescent label or the interactive dual label comprising a fluorescent reporter molecule and a quencher molecule is formed; wherein the extended duplex can be cleaved by (i) a restriction enzyme, wherein a cleavage site recognized by the restriction enzyme is present in the templating portion of the CTO; or (ii) a 5' to 3' exonuclease capable of cleaving the CTO of the extended duplex but not cleaving the CTO in a single-stranded state;

(e) forming a cleaved fragment by cleaving the extended duplex using the restriction enzyme or the 5' to 3' exonuclease if the target nucleic acid sequence is present in the DNA sample or the mixture of nucleic acids;

when the extended duplex has the single fluorescent label, the method is performed on a solid substrate on which the CTO is immobilized, the single fluorescent label is linked to the templating portion of the CTO, the cleaved fragment is with the single fluorescent label, and the cleaved fragment is released from the solid substrate; wherein when the CTO is immobilized through its 5'-end onto the solid substrate, the cleavage site for the restriction enzyme is located between the 5'-end of the CTO and the position of the single fluorescent label of the CTO, and when the CTO is immobilized through its 3'-end onto the solid substrate, the cleavage site for the restriction enzyme is located between the 3'-end of the CTO and the position of the single fluorescent label of the CTO;

when the extended duplex has said interactive dual label comprising a fluorescent reporter molecule and a quencher molecule, the quencher molecule of the CTO quenches a fluorescent signal from the fluorescent reporter molecule of the CTO prior to the formation of the hybridized complex of the step (c) and after formations of the hybridized complex of the step (c) and the extended duplex, the fluorescent reporter molecule and the quencher molecule of the CTO are separated by cleavage at the cleavage site of the CTO by the restriction enzyme or by sequential cleavage from the 5'-end of the CTO by the 5' to 3' exonuclease, wherein the cleavage site for the restriction enzyme is located between the fluorescent reporter molecule of the CTO and the quencher molecule of the CTO; and (f) detecting the target nucleic acid sequence from the DNA sample or the mixture of nucleic acids, wherein detecting a fluorescent signal from the single fluorescent label of the cleaved fragment or the fluorescent reporter molecule separated from the quencher molecule of the extended duplex indicates the presence of the target nucleic acid sequence in the DNA sample or the mixture of nucleic acids.

8. The method according to claim 7, wherein the method further comprises repeating the steps (a)-(b), (a)-(d), (a)-(e) or (a)-(f) after step (f).

\* \* \* \* \*